(12) United States Patent
Guy et al.

(10) Patent No.: US 7,693,573 B2
(45) Date of Patent: Apr. 6, 2010

(54) METHOD FOR NON-INVASIVELY DETERMINING THE RELATIVE LEVELS OF TWO BIOLOGICAL SUBSTANCES

(75) Inventors: Richard Henry Guy, Chef Lieu, Copponex (FR) F-74350; Maria Begona Delgado-Charro, Chef Lieu, Copponex (FR) F-74350

(73) Assignees: Richard Henry Guy (GB); Maria Begona Delgado-Charro (GB)

( * ) Notice: Subject to any disclaimer, the term of this patent is extended or adjusted under 35 U.S.C. 154(b) by 0 days.

(21) Appl. No.: 12/474,372

(22) Filed: May 29, 2009

(65) Prior Publication Data
US 2009/0281405 A1    Nov. 12, 2009

Related U.S. Application Data

(62) Division of application No. 10/481,676, filed on Dec. 19, 2003, now Pat. No. 7,555,337.

(30) Foreign Application Priority Data

Jun. 22, 2001    (EP)    ................... 01114750

(51) Int. Cl.
*A61N 1/30* (2006.01)
(52) U.S. Cl. ........................ 604/20; 600/345
(58) Field of Classification Search ................. 604/20; 600/345, 309
See application file for complete search history.

(56) References Cited

U.S. PATENT DOCUMENTS

| 5,279,543 A | 1/1994 | Cullander et al. |
| 5,730,714 A | 3/1998 | Glikfeld et al. |
| 6,059,736 A | 5/2000 | Tapper |
| 6,144,869 A | 11/2000 | Berner et al. |

FOREIGN PATENT DOCUMENTS

WO    96/00110 A    1/1996

OTHER PUBLICATIONS

International Search Report for PCT/EP02/06637; ISA/EPO; Mailed: Oct. 14, 2002.

*Primary Examiner*—Kevin C. Sirmons
*Assistant Examiner*—Deanna K Hall
(74) *Attorney, Agent, or Firm*—Harness, Dickey & Pierce, P.L.C.

(57) ABSTRACT

An iontophoretic sampling device for non-invasively determining the relative levels of two substances present in a biological system.

12 Claims, 23 Drawing Sheets

Combined Iontophoretic Sampling of Glutamate and Valproate

[Valproate] =21 µM to 104.5 µM

Figures 4a-b
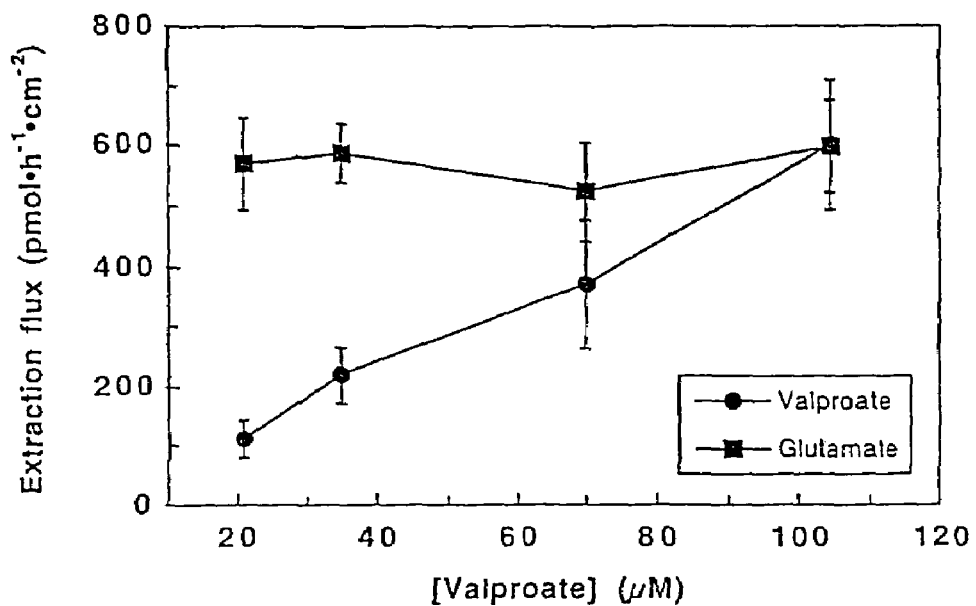
(a) Extraction fluxes of Valproate and Glutamate at 5 hours
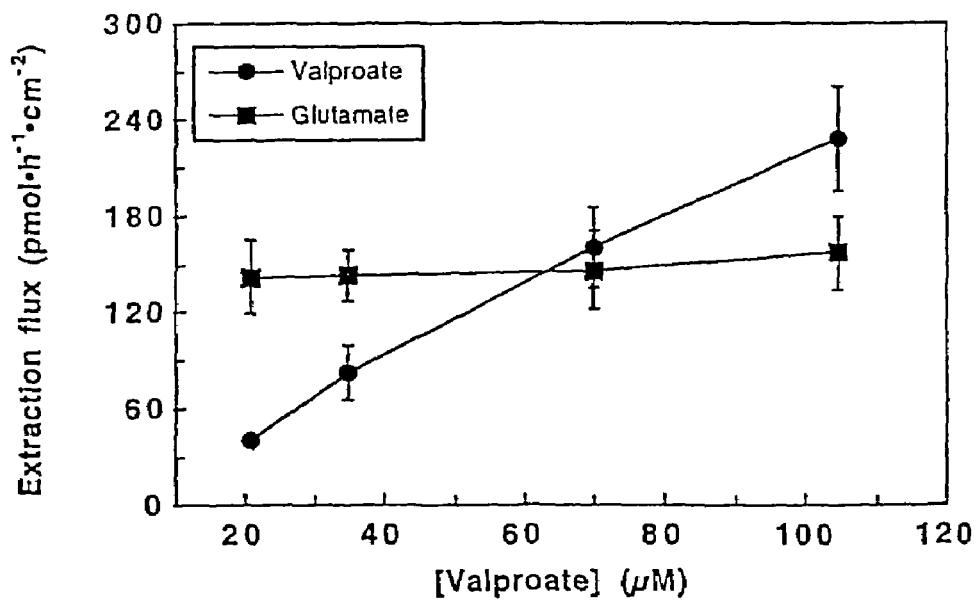
(b) Extraction fluxes of Valproate and Glutamate at 24 hours

Figures 5a-b
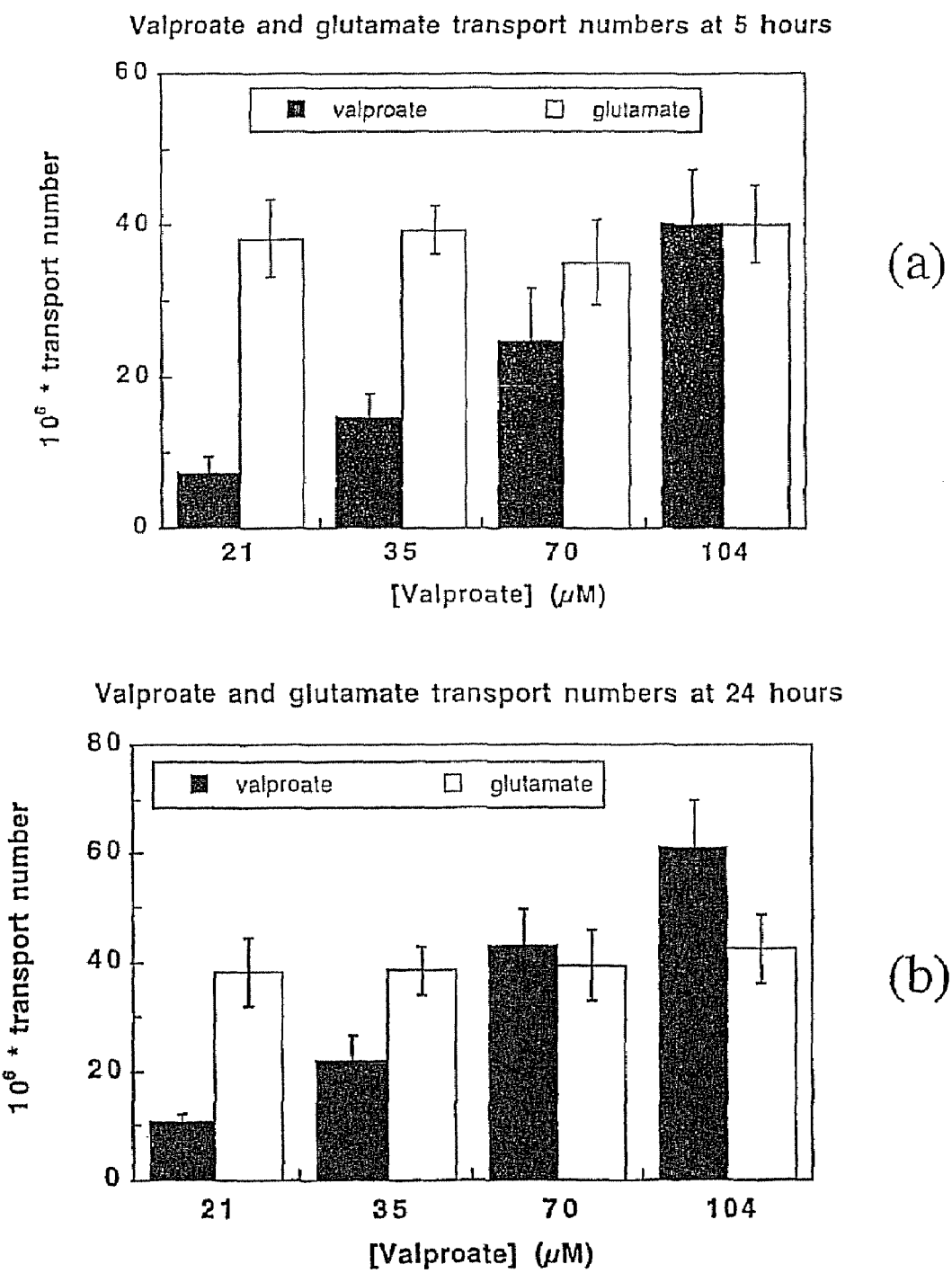

Figures 6a-b
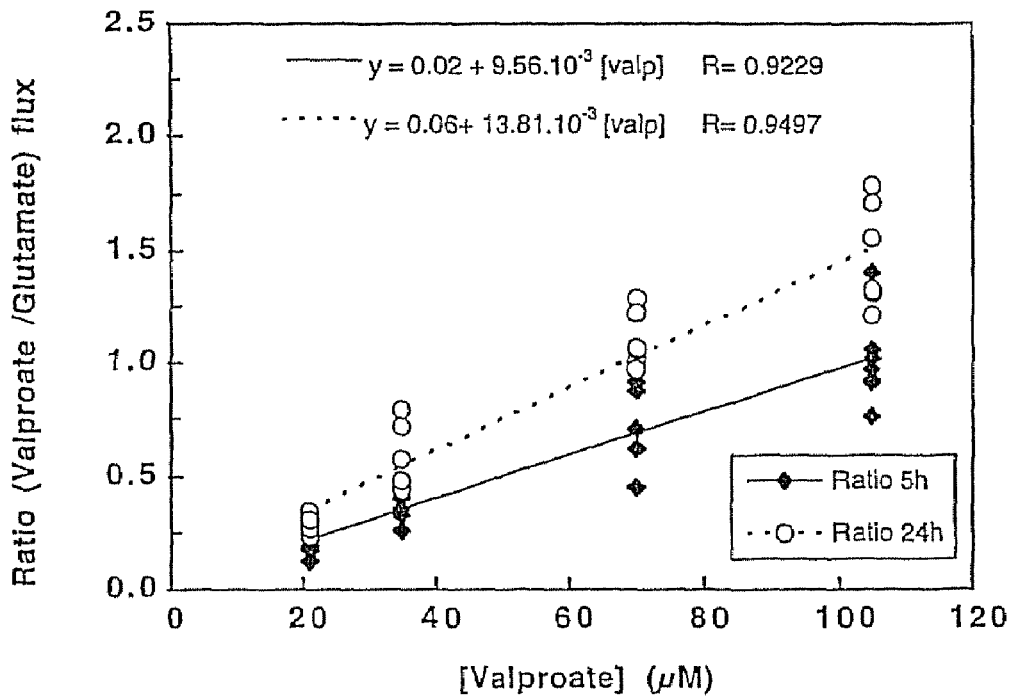
(a)
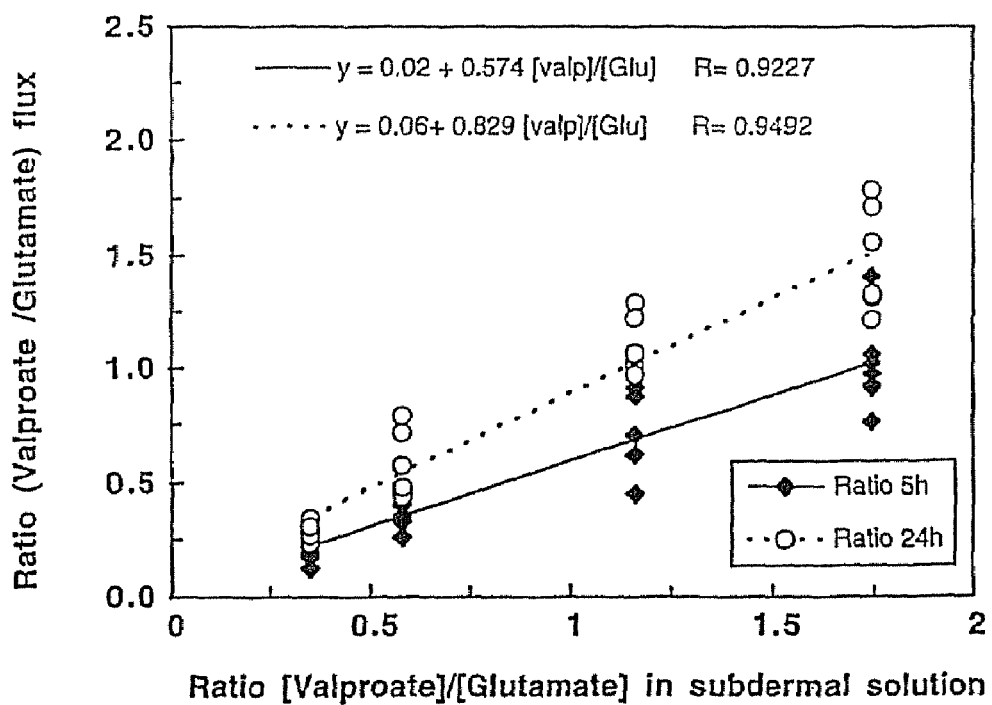
(b)

Combined Iontophoretic Sampling of Lactate, Ammonium, $K^+$, $Na^+$ and $Cl^-$.

Figures 8a-b
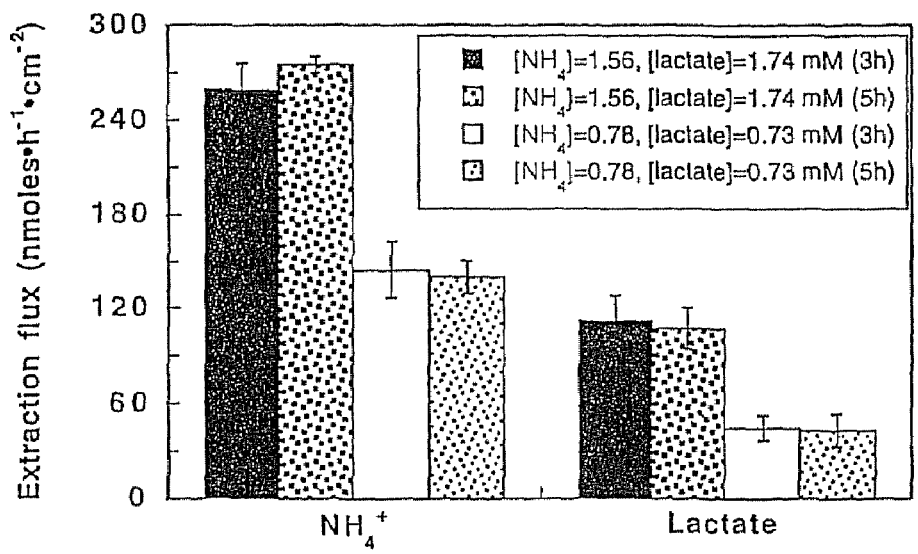
(a)
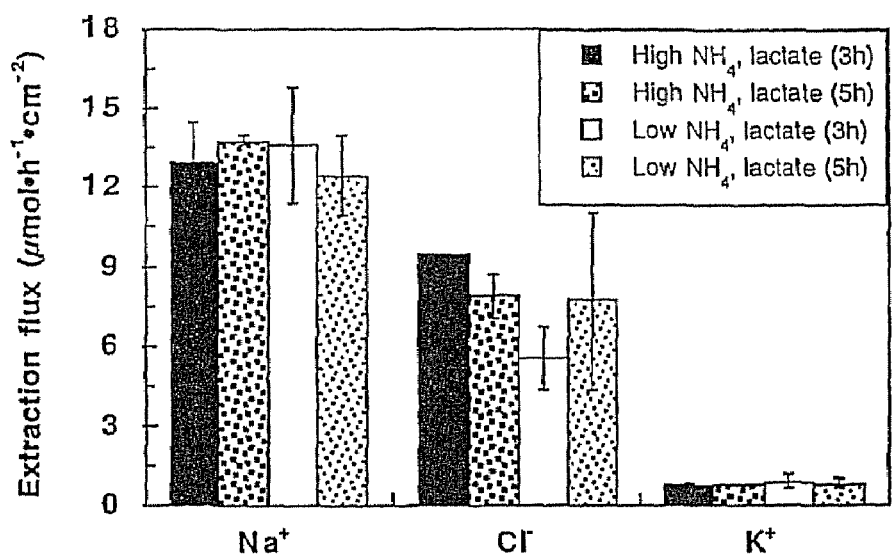
(b)

Figures 9a-b
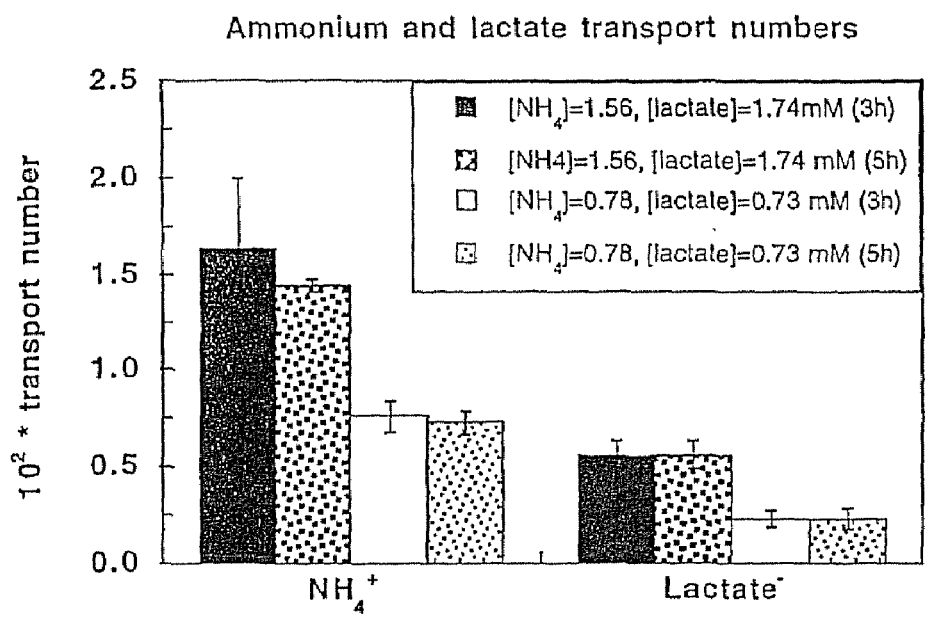
(a)
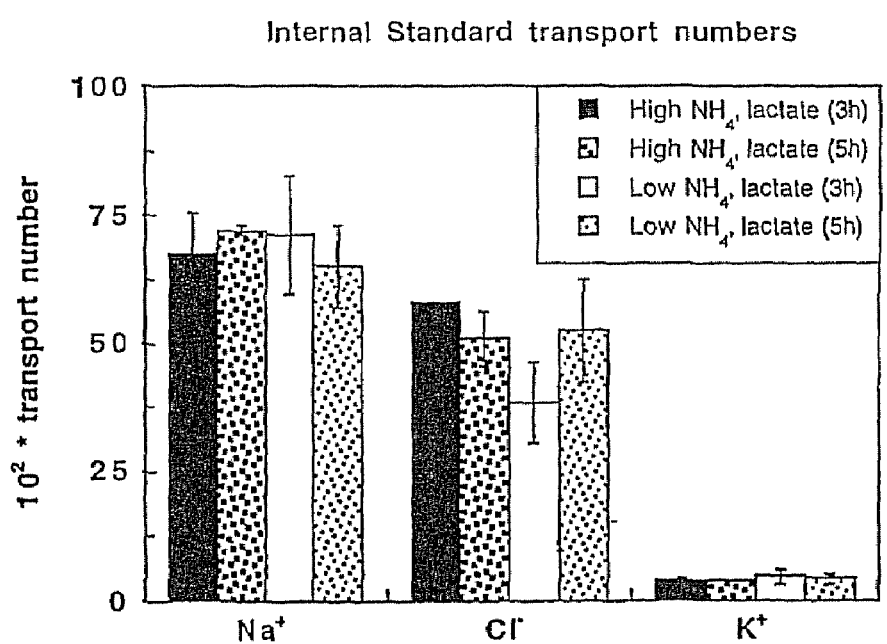
(b)

Figures 10a-b
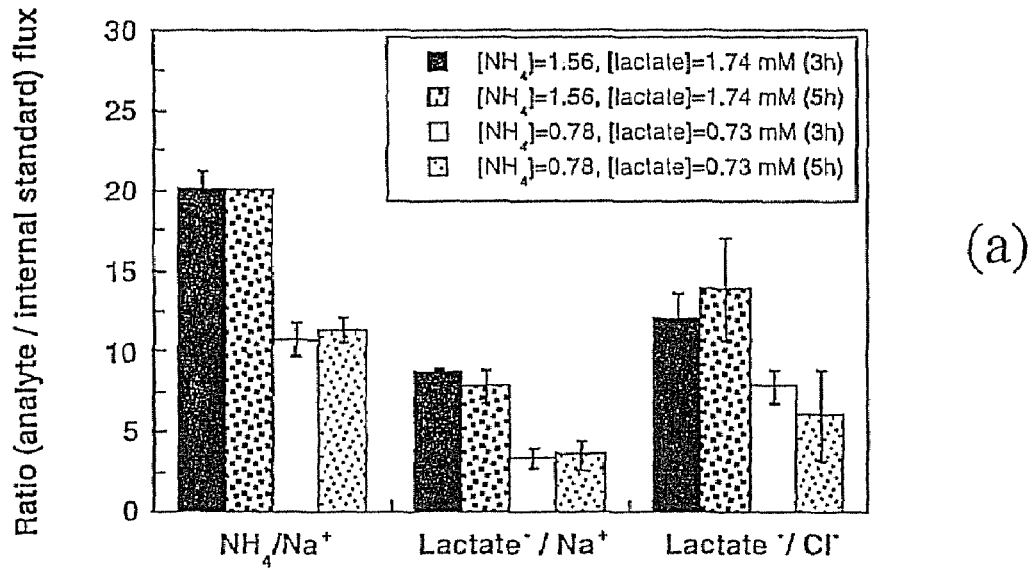
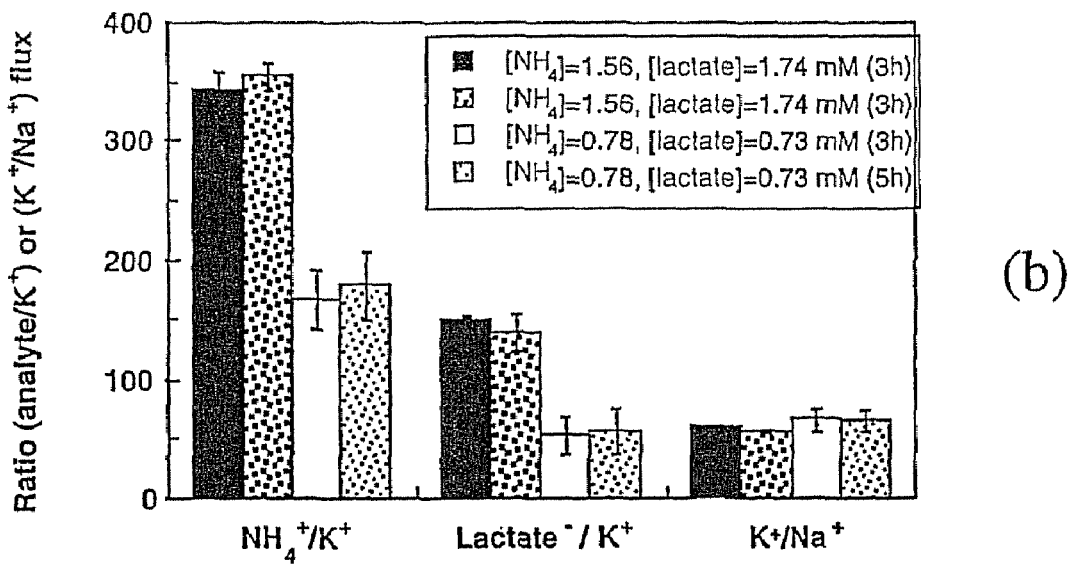

Figures 14a-b
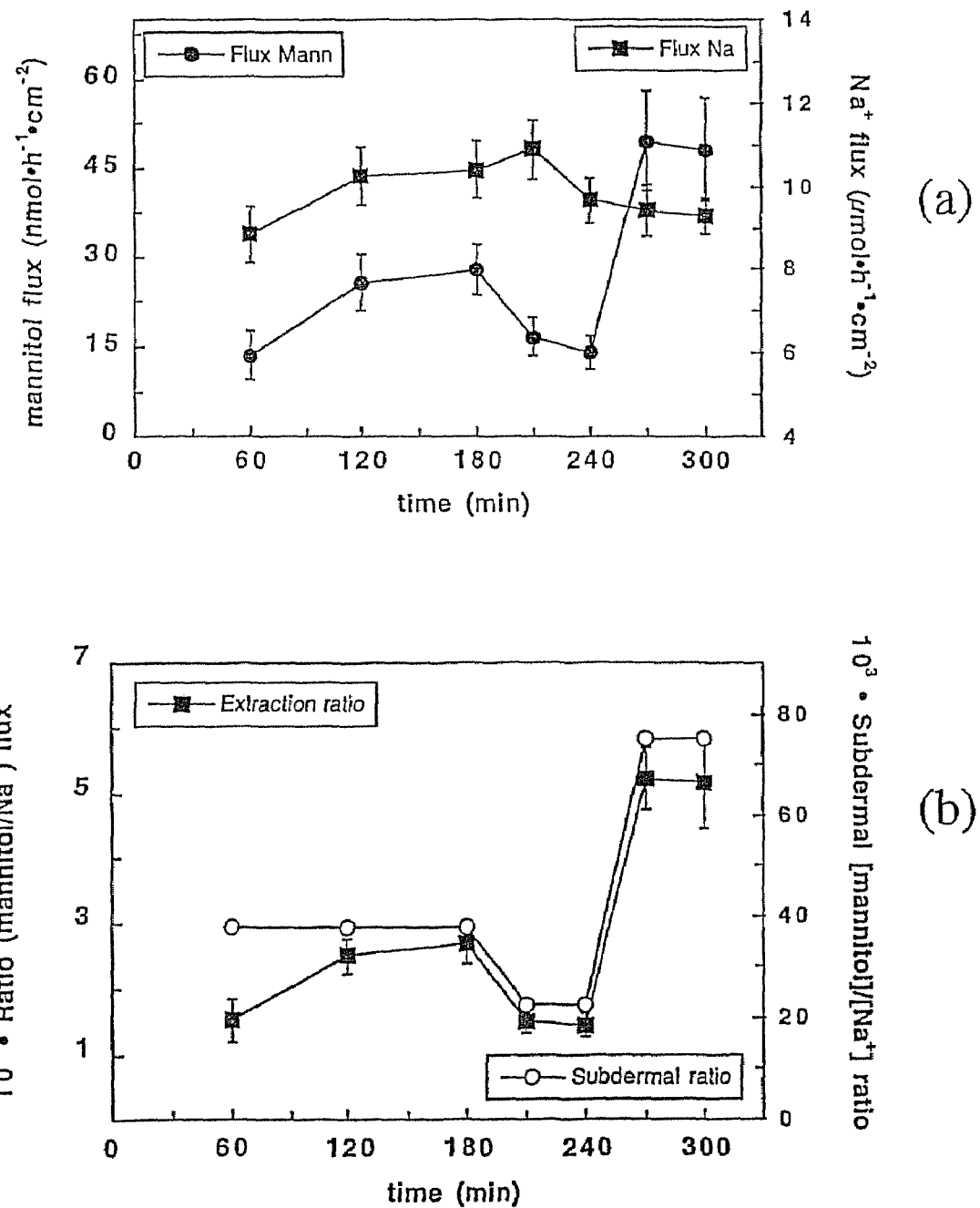

Figures 15a-b
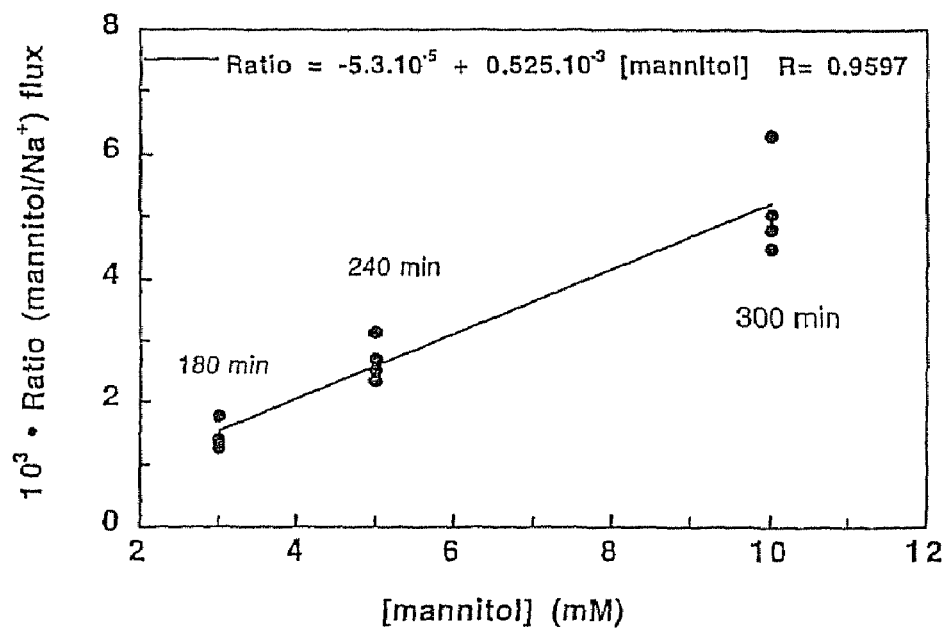
(a)
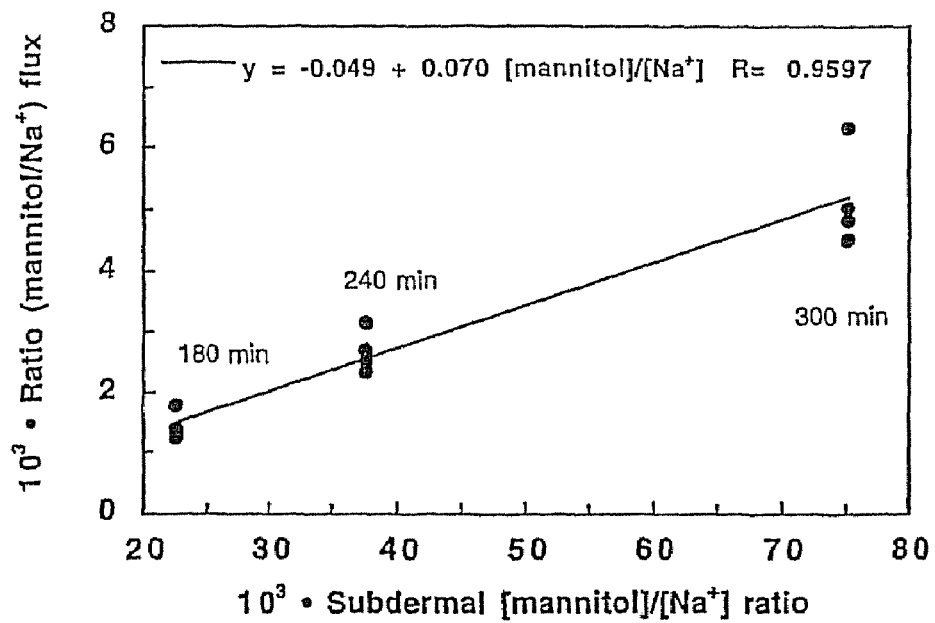
(b)

Combined Iontophoretic
Sampling of lithium and sodium

Figures 24a-b
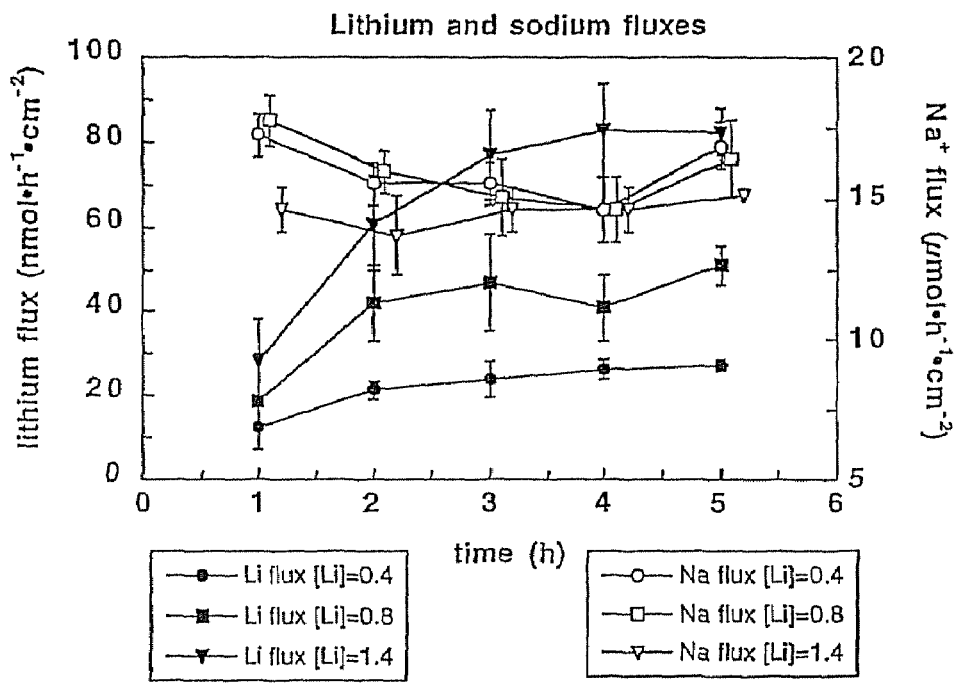
(a)
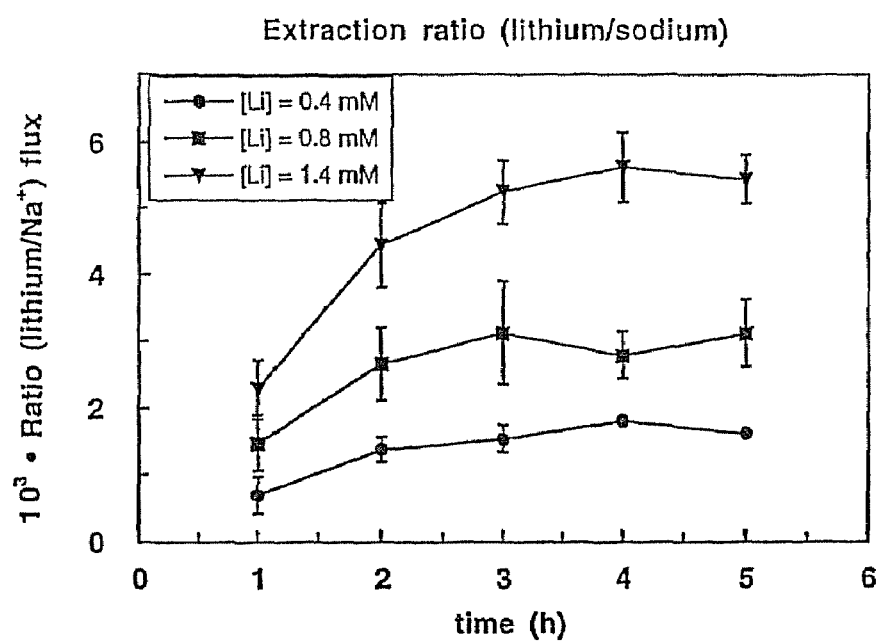
(b)

Figures 25a-b
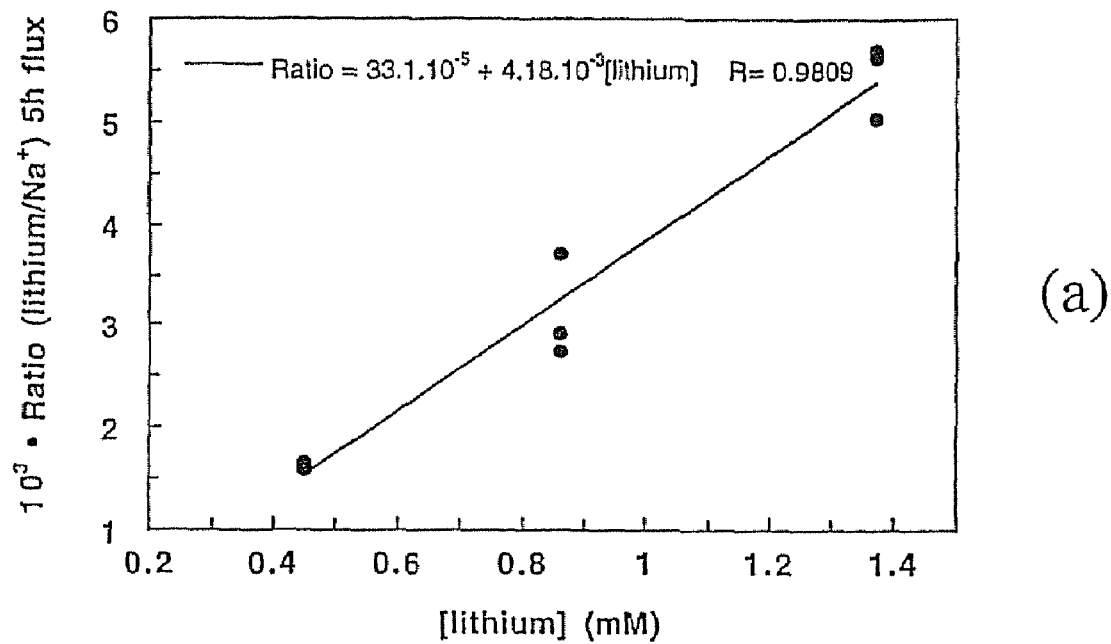
(a)
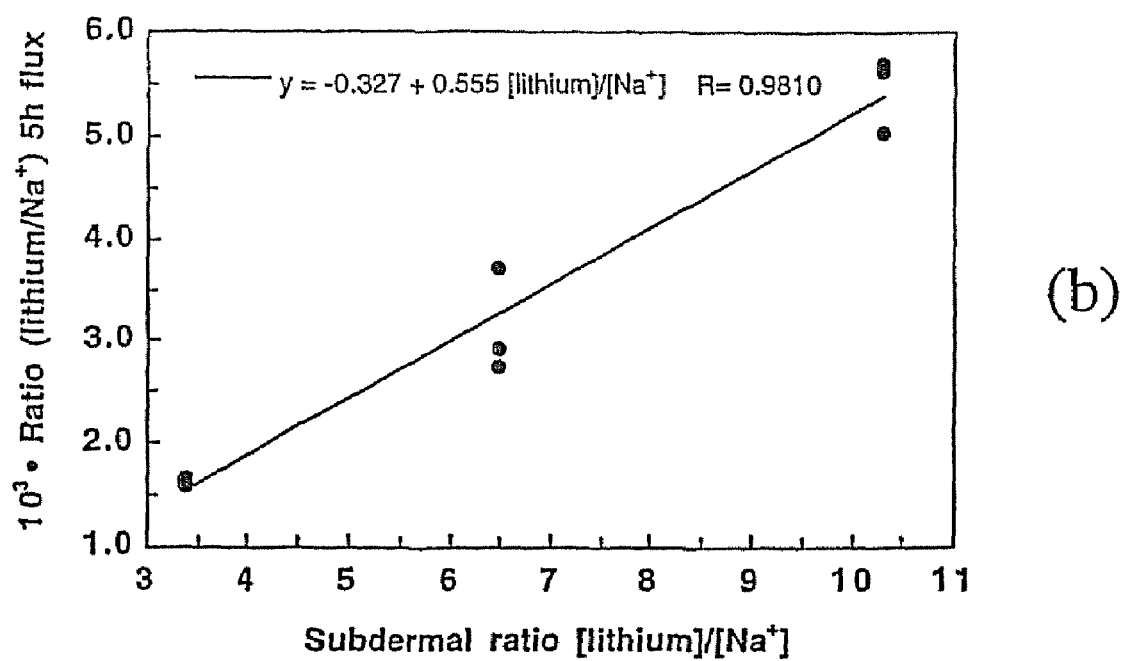
(b)

METHOD FOR NON-INVASIVELY DETERMINING THE RELATIVE LEVELS OF TWO BIOLOGICAL SUBSTANCES

RELATED APPLICATION

The present application is a divisional application of U.S. patent application Ser. No. 10/481,676 Dec. 19, 2003, now U.S. Pat. No. 7,555,337 issued Jun. 30, 2009.

FIELD OF THE INVENTION

The present invention concerns in a general manner a method for non-invasively determining the relative levels of two substances present in a biological system.

More particularly, the present invention relates to a method for determining the relative levels of two substances present in a biological system, using the technique of reverse iontophoresis, and to a iontophoretic sampling device for monitoring the relative levels of two substances present in a biological system.

DESCRIPTION OF THE RELATED ART

The detection and/or quantification of endogenous substances is a key factor in establishing a medical diagnosis.

Similarly, the detection and/or quantification of exogenous substances such as drugs, metabolites, and markers of therapeutic or toxic effect is a key factor to determine if a medical treatment is appropriate.

However, detection and/or quantification of endogenous or exogenous substances requires in a general manner a prior invasive blood sampling with a needle, with the consequences that pain may accompany the sampling procedure and there may be a risk of bacterial or viral infection for both patient and sampler.

An example where sampling of an endogenous substance is needed, at least several times a day for life time, is in the case of patients having sugar diabetes.

For these patients, real time information concerning the glucose levels in the body is most important information in the patient's treatment and in many cases, often a question of life or death.

A non-invasive method known under the name of iontophoresis has been used to achieve increased drug delivery across the skin for many years, and more recently it has been demonstrated that the symmetry of the procedure also allows samples of circulating, biologically-important ions and uncharged molecules dissolved in a biological fluid to be withdrawn from the subcutaneous space to the skin surface (a technique referred to generally as reverse iontophoresis).

The technique of iontophoresis may be defined as the enhanced transport of charged or uncharged molecules across biomembranes, in particular skin, under the influence of an electrical potential gradient.

The level of current necessary to enhance this transport is painless.

This technique avoids the need to puncture the skin and therefore reduces, tremendously, risks to both patient and sampler.

Iontophoresis uses a iontophoretic device consisting of a power supply and two electrode compartments.

These compartments hold an electrode and, typically, an electrolyte solution or conductive hydrogel.

In the case of iontophoretic sampling, the electrode compartments contain an appropriate receiving medium, for example buffered saline, into which the analytes of interest are collected.

The electrode compartments may also contain the means with which to quantify the analyte(s) of interest in situ, or the contents of the electrode compartment may be removed at certain predetermined times for determination of the analyte(s) in another apparatus.

Iontophoresis can be used successfully to withdraw, at significantly elevated levels, both charged and uncharged molecules from within and beneath the skin.

Iontophoretic transport through the skin involves two principal mechanisms.

One, so called electromigration, concerns only charged molecules and the other, so called electroosmosis or convective flow, can involve the transport of both charged and uncharged molecules.

The electromigrative transport is a direct consequence of the interaction of the electric field with ions.

When the electric field is applied, the cations contained in the anodal chamber are repelled from the anode toward and through the skin and the endogenous or exogenous cations are attracted into the cathodal chamber.

Consequently, an endogenous or exogenous cation will be collected into the cathodal chamber.

On the same principle, anions are repelled from the cathodal chamber and driven into and through the skin and the endogenous or exogenous anions are attracted into the anodal chamber on the skin surface.

Consequently, endogenous or exogenous anions will be collected into the anodal chamber.

The electroosmotic transport is based on the fact that, at neutral pH, the skin is a negatively charged membrane, and is therefore permselective to cations.

It follows that, on application of an electrical field, more charge is carried across the skin by positive ions than by negative ions.

This means that more momentum is transferred to the solvent (i.e., water) in the direction of cation movement so that uncharged molecules are convected along with the flow of solvent at a rate which is, for many substances, significantly greater than that possible by passive diffusion.

Consequently, an endogenous or exogenous uncharged molecule will be collected into the cathodal chamber.

Electroosmotic transport can be particularly efficient for water-soluble, polar (yet uncharged) substances, as these compounds typically have very poor permeability across the lipophilic (hydrophobic) skin barrier.

Further, the electroosmotic flow therefore assists the sampling of cations while diminishing, to some extent, the sampling of anions.

When the iontophoretic device is activated, an electrical circuit is established.

The exterior part of the circuit involves electrons travelling along the wire from the anode to the cathode via the power supply and the interior part of the circuit involves the movement of ions from one electrode chamber to the other via the skin and the physiological medium.

The number of electrons flowing in the exterior part of the circuit determines the number of ions moving in the interior part.

Hence, the flux of ions is directly proportional to the total charge in Coulombs passed between the electrodes from the power supply.

It is known that the extraction of a substance to the skin surface by reverse iontophoresis is proportional to the subcutaneous level of the substance.

Reverse iontophoresis per se is not selective so that discrimination comes at the level of the extracted sample.

Thus, a multiplicity of species can be withdrawn by iontophoresis and assayed specifically.

Based on these principles, U.S. Pat. No. 5,279,543, U.S. Pat. No. 5,362,307 and U.S. Pat. No. 5,730,714, disclose methods for non-invasively determining the level of a substance present in a biological system.

These methods comprise, in a general manner, contacting an anodal chamber and a cathodal chamber of an iontophoresis device with a biological system; extracting by reverse iontophoresis charged and uncharged substances from the biological system, and collecting said extracted substances into the anodal or cathodal chamber; analysing the collected amount of one of the extracted substances; and correlating the level of the analysed substance with a standard.

Based on these methods, U.S. Pat. No. 5,771,890, U.S. Pat. No. 5,989,409 and U.S. Pat. No. 6,023,629 disclose particular methods for measuring the concentration of a substance, in particular glucose, in a mammalian subject.

However, in these methods, the level of the analysed substance is correlated with the level of the substance in the blood of the patient, so that a blood sampling is required.

A number of devices for non-invasively determining the level of a substance present in a biological system based on these methods have been disclosed, most of them being provided for non-invasively monitoring glucose, as for example the device commercialised by Cygnus, Inc. (Redwood City, Calif., USA), under the name GlucoWatch® Biographer.

However, these devices must be calibrated each time they are started, and each calibration requires blood sampling.

In view of the above, there is a need for a method and for a device which does not require the comparison of the level of the iontophoretically extracted substance with a standard obtained from a blood sample and thus which would allow the monitoring of the level of a substance in a biological system without a calibration based on a blood sampling.

A preliminary study to ascertain whether tissue electrolytes may be determined by reverse iontophoresis was disclosed by F. B. Benjamin, R. Kempen, A. G. Mulder and A. C. Ivy. in *Journal of Applied Physiology*, vol. 6, pp. 401-407, 1954 "Sodium-potassium ratio of human skin as obtained by reverse iontophoresis".

Experiments were performed in vivo and in vitro.

In vivo, the situation of greatest interest, a metal plate cathode was used, being inserted into a lithium nitrate electrolyte solution (28.5 mEq/L) on the skin surface.

The area of contact between the cathode solution and the skin was 4.5 cm$^2$.

A current of 4 mA was passed for 5 minutes (and sometimes longer) and during this time, the pH of the lithium nitrate solution increased from 6.4 to 10.7, indicating hydrolysis of water at the cathode.

Skin damage was observed in some cases.

After current passage, the concentrations of potassium and sodium ions in the cathode chamber were typically about 14 and 35 µEq/L, respectively.

The day of the measurement, the ambient temperature, the gender and age of the subject, and the site of measurement on the body, did not affect significantly the results obtained.

The sodium to potassium ratio in the extraction solution was therefore about 2.5:1.

This ratio was compared to the relative composition of the ions in sweat (7.1:1), whole skin (6:1), epidermis (0.6:1), interstitial fluid (29:1) and intracellular fluid (0.03:1), and was clearly not consistent with any of these environments.

It was noted, however, that the extracted ratio did decrease in subjects receiving a low-sodium diet (to 2.0:1) and that it could also be lowered (again to 2.0:1) by blocking sweat secretion with atropine.

In neither case, though, did the ratio change to reflect the relative composition of the ions in any tissue of interest. Nor was any method provided that would allow the extracted ratio of ions to be related consistently to their relative composition in any tissue of interest.

In vitro, the extraction was performed with hypertonic, isotonic and hypotonic saline solutions below the excised skin obtained from a human cadaver.

The type of solution used influenced the extraction results in the same way as when similar solutions were injected intradermally in normal human subjects, in vivo.

Nevertheless, again, the ratio changes did not reflect quantitatively the relative composition of the ions in any tissue of interest. Nor was any method provided that would allow the extracted ratio of ions to be related consistently to their relative composition in any tissue of interest.

In summary, while this research purported to be useful for monitoring disturbances in electrolyte balance in patients, and speculated about the results being perhaps correlated with those of metabolic and blood concentrations, the results demonstrated in fact: (a) no agreement between the extracted sodium to potassium ratio and that in any tissue compartment of interest, and (b) no suggestion that either ion, or any other electrolyte or endogenous substance, for that matter, might be used as an internal standard for calibration-free, non-invasive biosensing by reverse iontophoresis.

More recently, an attempt has been made to determine the concentration of lactic acid on the dermal side of a iontophoretic cell by employing the flux ratio of lactic acid and chloride ions (the chloride ion being a constant level endogenous ion), as published by S. Numajiri, K Sugibayashi and Y. Morimoto in "Journal of Pharmaceutical & Biomedical Analysis Vol. 11, No. 10; pp 903-909, (1993) ("Non-invasive sampling of lactic acid ions by iontophoresis using chloride ion in the body as an internal standard").

In this document, the results show that chloride ion flux decreases with an increase in lactic concentration and that the flux ratio of lactic acid/chloride ions is constant and is independent of the electrical potential gradient thus meaning that the transport number of lactic acid is dependent on the transport number of chloride.

Since the flux ratio of lactic acid/chloride ions is constant, the flux ratio of lactic acid/chloride ions does not provide a direct measure of the relative levels of these two substances in the dermis side of the cell and further does not provide a direct measure of the physiological level of lactic acid in the dermis side of the cell.

Furthermore, in this document, two features of the experimental procedure used render the feasibility of the method at best questionable.

First, the level of current used to extract the ions of interest across the skin was either 2.1 mA/cm$^2$ or 3.2 mA/cm$^2$, that is, more than 4 or 6 times, respectively, the current density considered the maximum tolerable limit (0.5 mA/cm$^2$) for iontophoresis in vivo, in humans.

Second, platinum electrodes were utilised in the experiments reported.

It is well-established in the literature that the electrochemistry at platinum electrodes causes hydrolysis of water, liberating either hydronium cations or hydroxide anions into the electrode solutions with a considerable risk, therefore, of dramatic changes in pH.

Together with the high current densities used, as well, a significant probability of skin irritation and/or burns is evident from the procedure as described.

In addition, hydronium cations and hydroxide anions are small and very mobile, and they are efficient charge carriers in iontophoresis; their increasing presence in the electrode solutions will compete effectively with the ions of interest to carry charge across the skin, and will therefore further change the transport numbers of chloride and lactic acid ions, rendering useless the value of the method proposed.

An object of the present invention is to propose a method for determining the relative levels of two substances present in a biological system by avoiding blood sampling when only the relative concentration of two molecules is of interest.

A further object of the present invention is to propose a method wherein the relative levels of a first extracted substance present in a biological system with respect to a second extracted substance present in the biological system is a direct measure of the physiological level of the first substance, thus avoiding a calibration based on a blood sampling.

A still further object of the present invention is to propose a device which allows the monitoring of the relative levels of two substances present in a biological system without a calibration based on a blood sampling.

A still further object of the present invention is to propose a device which allows the monitoring of the physiological level of a substance present in a biological system without a calibration based on a blood sampling.

According to the present invention, these objects have been achieved as a result of the unexpected findings that when two substances extracted from a biological system by reverse iontophoresis have independent respective transport and/or transference numbers, the ratio of the respective extracted amounts or the ratio of their flux is a direct measure of the relative levels of the two substances in the biological system.

SUMMARY OF THE INVENTION

According to one aspect, the present invention concerns a method for non-invasively determining the relative levels of two substances present in a biological system, said method comprising:
  contacting an anodal chamber and a cathodal chamber of an iontophoresis device comprising reversible electrodes with a biological system;
  extracting by reverse iontophoresis charged and uncharged substances from said biological system, and collecting said charged and uncharged substances each independently into the anodal chamber or the cathodal chamber;
  analysing the collected amount of at least a first extracted substance and a second extracted substance; wherein said first and second substances are selected in such a way that the transport and/or transference number of the first substance is independent of the transport and/or transference number of the second substance;
  subsequently, determining the extraction ratio of the first substance to the second substance to determine their relative levels in the biological system.

According to the method of present invention, when the first substance and the second substance are both analytes susceptible to changes of their concentration in the biological system, the determined extraction ratio provides information about the relative concentrations of the two substances in the biological system.

In this case, the ratio may be advantageously used to establish a diagnostic of any physiological or pathological condition, in which the ratio of two endogenous or exogenous analytes is of relevance, without requiring a blood sampling.

Further, according to the method of the present invention, when the first substance is an analyte susceptible to changes in its concentration in the biological system and the second substance has a substantially constant concentration in the biological system, the second substance acts as an internal standard and the extraction ratio becomes a direct measurement of the physiological level of the first substance in the biological system.

In this case, the extraction ratio may be advantageously used to establish a diagnostic of any physiological or pathological condition, in which the physiological level of the endogenous or exogenous analyte is of relevance, without requiring a blood sampling.

According to a further aspect, the present invention provides a iontophoretic sampling device for non-invasively monitoring the relative levels of two substances present in a biological system, said device comprising:
  an electrical power supply,
  a collection assembly comprising a first collection chamber containing a first electroconductive medium in contact with a first electrode and a second collection chamber containing a second electroconductive medium in contact with a second electrode, said first and second electrodes being reversible electrodes and being each in contact with the electrical power supply when the collection assembly is inserted in the iontophoretic device;
  a means for analysing two or more selected charged and/or uncharged substances in either one or both of the collection chambers in order to determine their extracted amounts,
  a means for converting the extracted amounts of a first substance and a second substance to the extraction ratio of the first substance to the second substance, wherein said first and second substances are selected in such a way that the transport and/or transference number of the first substance is independent of the transport and/or transference number of the second substance.

According to the iontophoretic sampling device of the present invention, when the first substance and the second substance are both analytes susceptible to changes in their concentration in the biological system, the determined extraction ratio provides information about the relative concentrations of the two substances in the biological system.

In this case, the extraction ratio may be advantageously used to establish a diagnostic of any physiological or pathological condition, in which the ratio of two endogenous or exogenous analytes is of relevance, without requiring a blood sampling.

Further, according to the iontophoretic sampling device of the present invention, when the first substance is an analyte susceptible to changes in its concentration in the biological system and the second substance has a substantially constant concentration in the biological system, the second substance acts as an internal standard and the extraction ratio provides a direct measurement of the physiological level of the first substance in the biological system.

In this case, the extraction ratio may be advantageously used to establish a diagnostic of any physiological or pathological condition, in which the physiological level of the endogenous or exogenous analyte is of relevance, without requiring a blood sampling.

Other advantages of the present invention will appear in the following detailed description.

BRIEF DESCRIPTION OF THE DRAWINGS

FIGS. 4a-b represent the extraction fluxes of valproate and glutamate at 5 hours and 24 hours as obtained in the in vitro experiments reported in Example 1.

FIGS. 5a-b represent the transport numbers of valproate and glutamate at 5 hours and 24 hours as obtained in the in vitro experiments reported in Example 1.

FIG. 6a shows the linear correlation obtained between the extraction ratio (valproate/glutamate) and the valproate concentration in the sub-dermal solution as obtained in the in vitro experiments reported in Example 1.

FIG. 6b shows the linear correlation obtained between the extraction ratio (valproate/glutamate) and their molar ratio (valproate/glutamate) in the sub-dermal solution as obtained in the in vitro experiments reported in Example 1.

FIGS. 8a-b represent the extraction fluxes of lactate, ammonium, potassium, sodium and chloride at the $3^{rd}$ hour and $5^{th}$ hour of the experiments reported in Example 2.

FIGS. 9a-b represent the transport numbers of the two analytes of interest (lactate and ammonium) and of the three internal standards considered ($K^+$, $Na^+$ $Cl^-$) as obtained from the experiments reported in Example 2

FIGS. 10a-b represent the extraction ratio of the couples of substances [a] (ammonium/sodium), [b] (ammonium/potassium), [c] (lactate/chloride), [d] (lactate/sodium), [e] (lactate/potassium) and [f] (potassium/sodium] as obtained from the experiments reported in Example 2.

FIGS. 14a-b represent the fluxes of mannitol and sodium and the (mannitol/sodium) extraction flux ratio over the 5 hours of the experiments reported in Example 3, second experiment.

FIGS. 15a-b show the correlation between the iontophoretic extraction ratio of mannitol to sodium and [a] the mannitol sub-dermal concentration, and [b] the sub-dermal concentration ratio (mannitol/sodium) over the 5-hour period of the experiments reported in Example 3, second experiment.

FIGS. 24a-b show (a) the extraction fluxes of lithium and sodium and (b) the (lithium/sodium) extraction flux ratios, over the 5 hours of experiment reported in Example 7, for each sub-dermal lithium concentration considered.

FIGS. 25a-b show the correlation between the iontophoretic extraction ratio of lithium to sodium and [a] the lithium sub-dermal concentration, and [b] the sub-dermal concentration ratio (lithium/sodium) over the 5-hour period of the experiment reported in Example 7.

DETAILED DESCRIPTION OF THE INVENTION

The present invention will now be described in a more detailed manner, referring to FIGS. 1 and 2.

Formally, the method of the present invention may be divided in three distinct phases including:
  the extraction of charged and uncharged substances from a biological system by reverse iontophoresis including collection of these substances;
  the selection of at least two collected substances to be analysed and the analysis of said selected substances by using appropriate analytical chemistry techniques, to determine their respective extracted amounts;
  the determination of the extraction ratio of the two analysed substances, based on the analysis results to evaluate their relative levels in the biological system.

According to the method of the present invention the first phase of extraction and collection of the extracted substances includes the steps of
  contacting an anodal chamber and a cathodal chamber of an iontophoresis device comprising reversible electrodes with a biological system;
  extracting by reverse iontophoresis charged and uncharged substances from said biological system, and collecting said charged and uncharged substances each independently into the anodal chamber or the cathodal chamber.

A iontophoretic device which can be used in the method of the present invention may be any conventional iontophoretic device comprising a power supply connected to an anodal chamber and to a cathodal chamber, wherein said chambers contain each an appropriate receiving electroconductive medium provided to collect the substances of interest.

Figure 1:
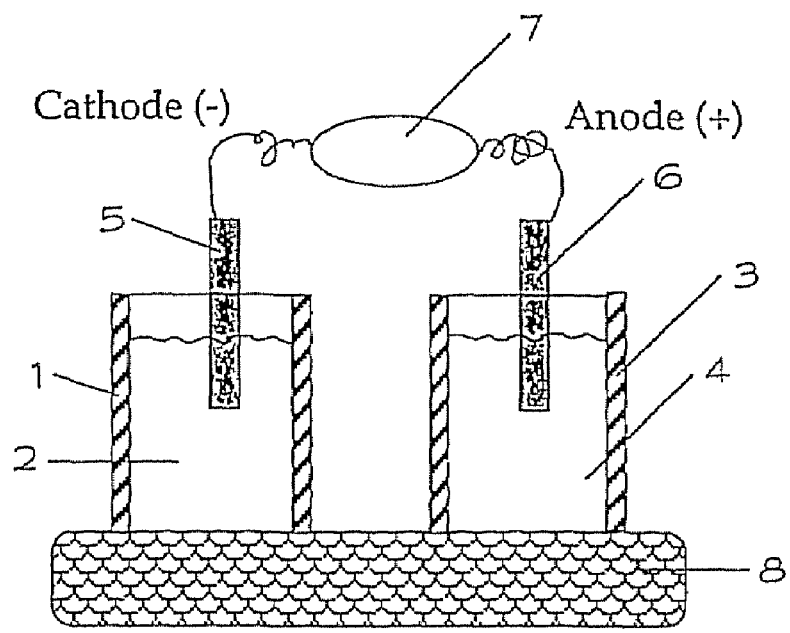
FIG. 1 shows a schematic view of a known iontophoretic device for use for in vivo sampling of charged or uncharged substances.

An example of a iontophoretic device which can be used for the extraction and the collection of the substances from a biological system according to the method of the present invention comprises, as represented schematically in FIG. 1, a first chamber 1 containing a first receiving electroconductive medium 2 and a second chamber 3 containing a second receiving electroconductive medium 4.

The receiving electroconductive media 2 and 4 may be each independently selected from a liquid, a gel, a paste, a sponge, a ceramic or a combination thereof.

A negative electrode or cathode 5 is immersed in the first receiving electroconductive medium 2 contained in the chamber 1 so that the chamber 1 is referred to as cathodal chamber 1.

A positive electrode or anode 6 is immersed in the second receiving electroconductive medium 4 contained in the chamber 3 so that the chamber 3 is referred to as anodal chamber 3.

The physical form of the electrodes (cylinder, sphere, disk, mesh, screen-printed, etc.) is chosen for convenience and practicality.

The cathode 5 and the anode 6 are each connected to a power supply 7 by wires.

The iontophoretic device used in the method of the present invention comprises reversible electrodes in order to avoid water hydrolysis.

More preferably, the iontophoretic device used in the method of the present invention comprises Ag/AgCl electrodes.

The anode and cathode electrode reactions are, respectively:

anode: $Ag^0(s)+Cl^-(aq) \rightarrow AgCl(s)+\acute{e}$

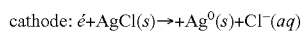
cathode: $\acute{e}+AgCl(s) \rightarrow +Ag^0(s)+Cl^-(aq)$ and are exactly opposite to one another.

Should it prove advantageous, therefore, to alternate the polarity of the electrodes during a reverse iontophoresis extraction procedure (as is the case, for example, in the GlucoWatch® Biographer of Cygnus, Inc.), the Ag/AgCl electrodes are ideal.

The cathodal chamber 1 and the anodal chamber 3 are each in close contact with a biological system 8.

Figure 2:
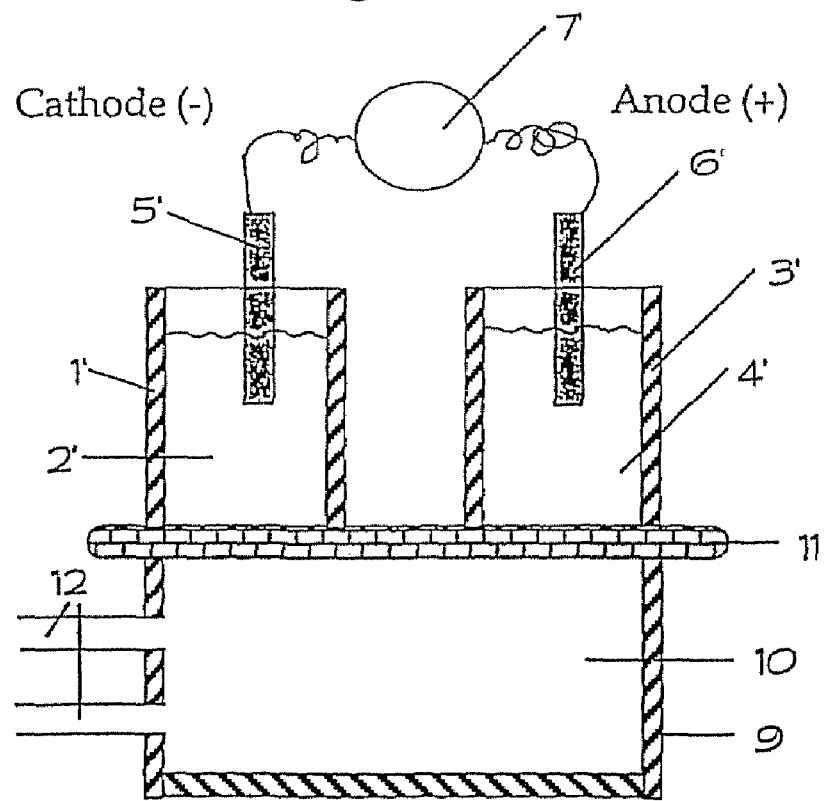
FIG. 2 shows a schematic view of a known iontophoretic device for the modeling in vitro of iontophoretic sampling of charged or uncharged substances.

The modeling in vitro of the extraction and collection of substances from a biological system according to the method of the present invention may be performed for example using the iontophoretic device represented schematically in FIG. 2, which comprises, similarly to the iontophoretic device represented in FIG. 1, a cathodal chamber 1' containing a first receiving electroconductive medium 2', an anodal chamber 3' containing a second receiving electroconductive medium 4', a cathode 5' immersed in the receiving medium 2' contained in the cathodal chamber 1', an anode 6' immersed in the receiving medium 4' contained in the anodal chamber 3', and a power supply 7' connected to both the cathode 5' and the anode 6'.

However, to simulate the biological system, this device, which will be referred to below as an in vitro iontophoretic device, will comprise, instead of the biological system, a container 9 containing an electroconductive donor solution 10 such as a physiological buffer containing the substances to be extracted, said container being closed in its upper part by a piece of a mammalian skin 11.

The container 9 may further comprise a circulation system 12 of the donor solution 10 to maintain constant, or to vary in a controlled fashion, the concentration of the substances contained in the donor solution 10.

In this in vitro iontophoretic device, the cathodal chamber 1' and the anodal chamber 3' are each in close contact with the mammalian skin 11.

Such devices are for example disclosed in U.S. Pat. No. 5,279,543, U.S. Pat. No. 5,362,307, U.S. Pat. No. 5,730,714, U.S. Pat. No. 6,059,736, U.S. Pat. No. 5,771,890, U.S. Pat. No. 6,023,629.

In the method of the present invention, the cathodal chamber 1 containing the first receiving electroconductive medium 2 and the anodal chamber 3 containing the second receiving electroconductive medium 4 of the iontophoretic device as represented in FIG. 1 are first contacted with the biological system 8.

Preferably, the biological system is a human body so that the cathodal chamber 1 and the anodal chamber 3 will be in contact with skin or mucosal tissues.

Then a current is applied during a determined time by means of the power supply 7 to establish an electric circuit.

According to the present invention, the current density may range from 0.01 to 1.00 mA/cm², depending on the biological system.

Preferably, the current density should not be higher than 0.5 mA/cm² when the biological system is a human body, since levels higher than 0.5 mA/cm² may cause unpleasant sensation or pain.

A more preferred current density applied when the biological system is a human body is about 0.3 mA/cm².

The exterior part of the circuit involves electrons travelling along the wire from the anode 5 to the cathode 6 via the power supply 7 and the interior part of the circuit involves the movement of ions from one electrode chamber to the other via the biological system 8.

Thus, due to this circuit, cations move from the anode 6 to the cathode 5 via the biological system 8 under a mechanism of electromigrative transport assisted by electroosmotic transport, anions move from the cathode 5 to the anode 6 via the biological system 8 under a mechanism of electromigrative transport, and counter to electroosmotic flow, and uncharged molecules move in same direction as the cations from the anode 6 to the cathode 5 via the biological system 8 under electroosmotic transport.

As a consequence, cations are extracted from the biological system 8 and are collected into the cathodal chamber 1, anions are extracted from the biological system 8 and are collected into the anodal chamber 3, and uncharged substances are extracted from the biological system 8 and collected into the cathodal chamber 1.

An advantageous effect of extracting substances by reverse iontophoresis is that the collected samples are free of proteins and of various cellular or tissue debris because proteins and various debris are blocked by the skin and retained in the biological system.

Similarly, an in vitro iontophoretic device as represented by FIG. 2 may be used for modeling the extraction and the collection of substances according to the method of the present invention.

In this case, cations are extracted from the donor solution 10 across the piece of mammalian skin 11 and are collected into the cathodal chamber 1', anions are extracted from the donor solution 10 via the piece of mammalian skin 11 and are collected into the anodal chamber 3', and uncharged substances are extracted from the donor solution 10 across the piece of mammalian skin 11 and are collected into the cathodal chamber 1'.

As iontophoresis per se is not selective, iontophoretic extraction leads to the collection of a number of different molecules including ions and uncharged molecules dissolved in the biological system.

After the first phase of extraction of charged and uncharged substances from the biological system by reverse iontophoresis and the collection of these extracted substances in the collection chambers 1 and 3; the method of the present invention comprises the second phase of selection of two extracted substances for which the extraction ratio is to be determined, and the analysis of these two collected substances using appropriate analytical chemistry techniques including the use of specific biosensors and biosensing methods to determine their respective extracted amounts.

Since iontophoresis per se is not selective, discrimination of the pair of substances for which the relative levels in the biological system are to be determined is achieved at the level of the analysis of the collected substances.

Accordingly, the second phase of the method of the present invention comprises the step of analysing the collected amount of a first extracted substance and of a second extracted substance.

According to the present invention, an essential feature is that the first and second substances must be selected in such a way that the transport and/or transference number of the first substance is independent of the transport and/or transference number of the second substance.

In the present invention, the pair of substances whose relative levels are to be determined is selected depending on the desired objectives.

If only the relative concentration of the two substances in the biological system is of interest, the first substance and the second substance may be selected to be both susceptible to changes in their concentration.

In this case, the extraction ratio only provides information about the relative systemic concentrations, not about the respective "real" concentrations.

An advantageous use of such a selection may be for example when the ratio between two molecules may give indications of a pathologic state or a disease.

However, in a particularly preferred embodiment of the invention, the first substance is selected to be a substance of interest susceptible to changes in its concentration in the biological system and the second substance is selected to have a substantially constant concentration in the biological system and consequently a substantially constant iontophoretic extraction flux so that the extraction ratio between the first substance and the second substance varies essentially linearly with the concentration of the first substance.

In this case, the second substance acts as a physiological internal standard and the extraction ratio becomes a direct measurement of the physiological level of the first substance (analyte) in the biological system.

This may be explained as follows.

The iontophoretic flux of a substance included in a ionic solution such as the physiological medium is proportional to the concentration of that substance.

It follows that the iontophoretic flux of the internal standard remains practically constant.

On the other hand, the extraction of the analyte will vary according to its concentration in the body.

It follows that the ratio of the extracted substances should be proportional to their relative internal concentrations.

This advantageous embodiment allows determination of the real concentration of the analyte in the biological system while avoiding blood sampling, as illustrated below.

In a preferred embodiment, the first substance and the second substance are collected in the same collection chamber.

This preferred embodiment is achieved when the first substance and the second substance are either two anions, or two cations, or one neutral molecule and one cation, or two neutral molecules.

For example, according to this preferred embodiment, monitoring of the concentration of glucose, a neutral molecule, as the analyte may be performed by using sodium, a cation, as the physiological standard, thus avoiding the sampling of blood several times a day for patients having sugar diabetes.

However, in the case where the first substance is an analyte and the second substance is an internal standard, and that the analyte and the internal standard are an anion and a cation, or an uncharged molecule and an anion, this preferred embodiment may be achieved by reversing the polarity of the current applied.

However, it should be noted that reversing polarity may be also used when the analyte and the internal standard are either two anions, or two cations or one neutral molecule and one cation.

As an example of an iontophoretic extraction wherein polarity is reversed during the extraction procedure, current is first applied as disclosed above during a first determined time by means of the power supply 7 to establish the electric circuit.

As a consequence, cations are collected into the cathodal chamber 1, anions are collected into the anodal chamber 3, and uncharged substances are collected into the cathodal chamber 1.

Then, the polarity is reversed and current is applied during a second determined time to establish an inverted electric circuit, wherein the electrode 5 becomes an anode, and the electrode 6 becomes a cathode.

Thus, due to this inverted circuit, the cations move from the electrode 5 to the electrode 6 via the biological system 8, the anions move from the electrode 6 to the electrode 5 via the biological system 8 and the uncharged molecules move in same direction as the cations from the electrode 5 to the electrode 6 via the biological system 8.

This means that due to this inversion of polarity, cations are collected into the collection chamber 3, anions are collected into the collection chamber 1, and uncharged substances are collected into the collection chamber 3.

As a consequence, cations and uncharged molecules and then anions are collected sequentially into the chamber 1, anions and then cations and uncharged molecules are collected sequentially into the chamber 3.

Advantages to collect the analyte and the internal standard in the same electrode chamber are to assure that the extraction of the two substances (analyte and internal standard) occurs across exactly the same skin surface and to obviate any problems associated with site-to-site differences in the properties of the skin; and to allow all the electro- and analytical chemistries necessary to be contained within the one chamber.

Further, if reversing the polarity is used between each iontophoresis/analysis cycle, then both electrode formulations can be identical, facilitating the manufacturing/assembly process; and similarly, with reversing polarity and Ag/AgCl electrodes, there is no concern about build-up or depletion of AgCl at the anode and cathode during the course of the procedure.

Further, if continuous monitoring is not required, and analysis is performed "off-line", having both substances collected into the same receiver simplifies subsequent processing.

Analysis of both the selected substances is performed using appropriate analytical techniques including biosensing techniques to determine the amount of each extracted selected substance.

For example, the means of analysing both selected substances may involve specific enzymes, ion-selective chemistry, measurement of conductivity and all other known analytical chemistry techniques of sufficient specificity, sensitivity and precision.

The third phase of the method according to the present invention is to determine the relative levels of the two selected analysed substances, based on the analysis results.

The determination of the extraction ratio of the first substance to the second substance may be made either by calculating the ratio of the collected amount of the first extracted substance in a predetermined period of time to the collected amount of the second extracted substance in the same predetermined period of time, in particular when the first substance and the second substance are extracted simultaneously, or in any case, by first calculating the flux of the first extracted substance and of the second substance, based on the extracted amounts of the first substance and of the second substance, respectively, and then by calculating the ratio of the flux of the first extracted substance to the flux of the second extracted substance.

It should be noted that, in the present invention, since a number of substances are extracted due to the non-selectivity of the iontophoretic extraction, more than two substances may be analysed to determine their extracted amount; thus, one iontophoretic extraction allows the determination of the extraction ratio of two substances for more than one pair of extracted substances.

Thus, according to the present invention, if more than two substances are analysed, multiple extraction ratios may be determined.

In one embodiment, the ratio of the extracted amounts or the ratio of the extracted fluxes of the first substance A ($Q_a$) and the second substance B ($Q_b$) directly reflects their relative concentrations in the biological system ([A]/[B]), i.e., $$Q_a/Q_b = K \cdot \{[A]/[B]\} \quad \text{(equation 1)}$$

where K is a constant.

This embodiment is advantageous when the ratio of A to B in the biological system is indicative, for example, of the development of a particular pathological state.

It follows that a change in $Q_a/Q_b$ directly reflects the same relative change in [A]/[B] in the biological system.

In a second embodiment, when substance B is selected so that, in a population, [B] is invariant, a change in $Q_a/Q_b$ directly reflects the corresponding change in [A].

In other words, $$Q_a/Q_b = K' \cdot [A] \quad \text{(equation 2)}$$

where $K' (=K/[B])$ is a constant.

This embodiment is advantageous when it is known that a change in the value of [A] by a certain percentage, up or down, poses a medical risk (e.g., a drug level too low for effect or too high and potentially toxic), or indicates a need for alternative therapeutic intervention.

In another embodiment, equations (1) and (2) are particularly useful when substance B is selected so that, in a population, [B] is invariant and can be considered constant, and K (and hence K') is known.

In this case, the measured ratio $Q_a/Q_b$ can be directly converted into the concentration of A ([A]) in the biological system, without the need to calibrate with a blood sample.

Examples of couples of analyte/internal standard which may be applied in the present invention are lithium/potassium, lithium/sodium, lactate/chloride, lactate/sodium, lactate/potassium, glucose/sodium, glucose/potassium, ammonium/sodium, ammonium/potassium, potassium/sodium, ethanol/sodium, ethanol/potassium, valproate/chloride, valproate/potassium, valproate/sodium, these examples of course not being limited to these couples.

Certain examples below will show how substance B may be selected and how K (and hence K') may be determined in order that this embodiment be practical.

The present invention also provides a iontophoretic sampling device for non-invasively monitoring the relative levels of two substances present in a biological system, this device being conceived to provide information on the relative levels of two substances or preferably information on the physiological level of one substance to a patient who would wear the device at a convenient location, such as the wrist.

The iontophoretic sampling device according the present invention applies the method according to the present invention so that the above description in relation with the method may be considered in a general manner for the device.

The iontophoretic sampling device according to the present invention comprises, as for the iontophoretic device represented schematically in FIG. 1, an electrical power supply, a collection assembly comprising a first collection chamber containing a first electroconductive medium in contact with a first electrode and a second collection chamber containing a second electroconductive medium in contact with a second electrode, said electrodes being reversible electrodes, preferably silver/silver chloride electrodes, and being each in contact with the electrical power supply when the collection assembly is inserted in the iontophoretic device.

Further, this device according to the present invention comprises a means for analysing automatically two or more selected charged and/or uncharged substances in either one or both of the collection chambers in order to determine their extracted amounts.

For example, the means of analysing both the selected substances may involve specific enzymes, ion-selective chemistry, measurement of conductivity and all other known analytical chemistry techniques of sufficient specificity, sensitivity and precision.

Further, the device according the present invention comprises a means for converting the extracted amounts of a first substance and a second substance to the extraction ratio of the first substance to the second substance, wherein said first and second substances are selected in such a way that the transport and/or transference number of the first substance is independent of the transport and/or transference number of the second substance.

According to an embodiment, the means for converting the extracted amounts of a first substance and a second substances to the extraction ratio of the first substance to the second substance is a programmable means able to calculate the ratio of the collected amount of the first extracted substance to the collected amount of the second extracted substance.

In another embodiment, the means for converting the extracted amounts of a first substance and a second substance to the extraction ratio of the first substance to the second substance is a programmable means able to first calculate the fluxes of the first extracted substance and of the second substance, based on the extracted amounts of the first substance and of the second substance, respectively, and then to calculate the ratio of the flux of the first extracted substance to the flux of the second extracted substance.

The iontophoretic sampling device according to the present invention may be conceived to provide information on the relative levels of the first substance to the second substance when the first and second substances for which the extraction ratio is to be determined are susceptible to changes in their concentration in the biological system.

Further, the iontophoretic sampling device according to the present invention may be conceived to provide information on physiological concentration of the first substance when the first substance is susceptible to changes in its concentration in the biological system and the second substance has a substantially constant concentration in the biological system, the physiological concentration of the first substance being determined based upon the constant physiological concentration of the second substance.

The iontophoretic device according to the present invention may further comprise a means to reverse the electrode polarity subsequent to each extraction/analysis cycle.

In a particularly preferred embodiment, the iontophoretic sampling device according the present invention is miniaturised to be worn on a person's body.

Such a miniaturised form may be, for example, conceived to be worn on the wrist by a patient.

Such a miniaturised device may be used for example to monitor the physiological level of glucose present in diabetic patient, without a calibration based on a blood sampling, since the physiological concentration of the glucose would be determined based upon the constant physiological concentration of a second substance, for example sodium ion, acting as an internal standard.

The invention will be now further explained in more detail with the following Examples referring to FIGS. 3-25.

EXAMPLES

Example 1

Figure 3:
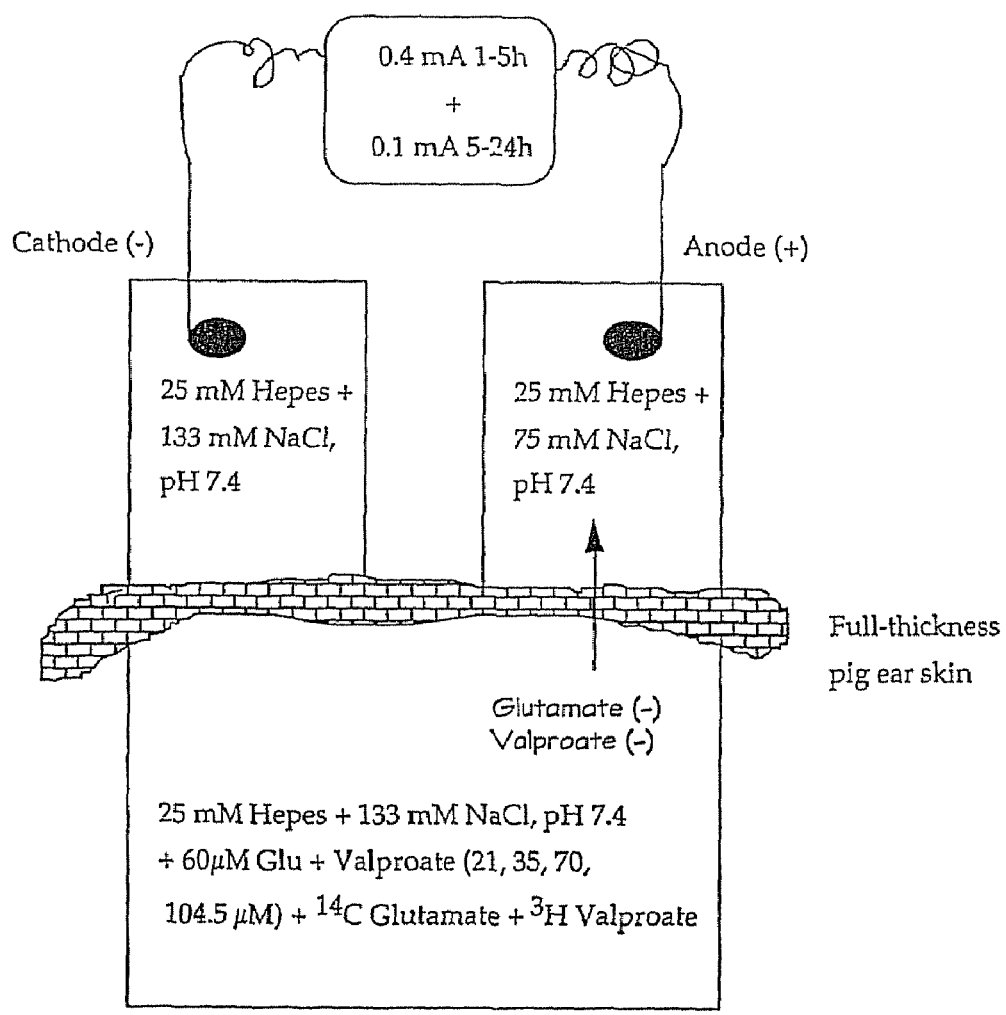
FIG. 3 represents a specifically-designed iontophoresis cell used for the in vitro experiments reported in Example 1.

A series of in vitro experiments was performed in specifically-designed iontophoresis diffusion cells (Laboratory Glass Apparatus, Berkeley, Calif., USA) as represented in FIG. 3.

The sub-dermal (donor) solution was a pH 7.4 buffer (25 mM Hepes+133 mM NaCl) to which 60 µM glutamate was added as an internal standard.

The analyte of interest was the anti-epileptic drug valproate, which was included at 4 different concentrations: 21 µM, 35 µM, 70 µM and 104.5 µM.

To facilitate the analytical chemistry, the donor solution was spiked with tritiated valproate and with $^{14}$C-labeled glutamate.

The anodal and cathodal chambers contacted the outer surface of the skin and contained the receptor (collection) media, respectively, 75 mM NaCl+25 mM Hepes and 133 mM NaCl+25 mM Hepes (both buffered at pH 7.4).

Full-thickness pig-ear skin was clamped between the two halves of the iontophoresis cell and each chamber filled with the appropriate solution.

A schema of the experiment is shown in FIG. 3.

A current of 0.4 mA (0.5 mA/cm$^2$) was passed between silver-silver chloride, (Ag/AgCl) electrodes, inserted into the anodal and cathodal chambers, for a total of 5 hours.

Every hour, the entire content of the anode solution was withdrawn and the chamber refilled with fresh buffer.

The cathodal chamber was sampled only at the end of 5 hours of current passage.

Subsequent to this first period of 5 hours at 0.4 mA, a reduced current of 0.1 mA was passed for the next 19 hours, at the end of which both anodal and cathodal chambers were sampled.

The total experiment therefore lasted 24 hours.

All samples were analyzed for glutamate and valproate by liquid scintillation counting.

At least 6 replicates were performed for each valproate concentration.

The results showed, as expected, that both valproate and glutamate (which are negatively charged) were extracted at the anode.

Table I shows the extraction flux of both anions for each sampling time and for each valproate concentration.

FIGS. 4a-b present the results measured at 5 and 24 hours.

Valproate extraction fluxes increased with concentration, while the flux of glutamate remained the same for all experiments and was independent of valproate concentration.

TABLE I

Extraction fluxes (pmoles · h$^{-1}$ · cm$^{-2}$) of valproate and glutamate for each sampling period. Glutamate concentration was always 60 µM. The current was 0.4 mA during the first 5 hours and 0.1 mA during the next 19 hours. Values are given as mean (±standard deviation).

| | [Valproate] = 21 µM | | [Valproate] = 35 µM | | [Valproate] = 70 µM | | [Valproate] = 104.5 µM | |
|---|---|---|---|---|---|---|---|---|
| Time (h) | Valproate flux | Glutamate flux | Valproate flux | Glutamate flux | Valproate flux | Glutamate flux | Valproate flux | Glutamate flux |
| 0-1 | 18 (±12) | 118 (±67) | 42 (±19) | 155 (±82) | 53 (±29) | 88 (±45) | 120 (±65) | 148 (±63) |
| 1-2 | 50 (±17) | 308 (±118) | 113 (±32) | 367 (±87) | 185 (±83) | 267 (±103) | 313 (±100) | 361 (±71) |
| 2-3 | 79 (±22) | 440 (±110) | 161 (±40) | 484 (±85) | 268 (±99) | 388 (±94) | 440 (±108) | 490 (±54) |
| 3-4 | 92 (31) | 479 (±86) | 202 (±50) | 571 (±42) | 342 (±114) | 494 (±102) | 531 (±128) | 566 (±74) |

TABLE I-continued

Extraction fluxes (pmoles · h$^{-1}$ · cm$^{-2}$) of valproate and glutamate for each sampling period. Glutamate concentration was always 60 μM. The current was 0.4 mA during the first 5 hours and 0.1 mA during the next 19 hours. Values are given as mean (±standard deviation).

| Time (h) | [Valproate] = 21 μM | | [Valproate] = 35 μM | | [Valproate] = 70 μM | | [Valproate] = 104.5 μM | |
|---|---|---|---|---|---|---|---|---|
| | Valproate flux | Glutamate flux | Valproate flux | Glutamate flux | Valproate flux | Glutamate flux | Valproate flux | Glutamate flux |
| 4-5 | 112 (±30) | 570 (±77) | 220 (±47) | 588 (±49) | 369 (±106) | 524 (±82) | 600 (±108) | 599 (±77) |
| 5-24 | 41 (±4) | 142 (±23) | 82 (±17) | 143 (±16) | 160 (±25) | 146 (±24) | 228 (±33) | 157 (±23) |

Table II and FIGS. 5a-b show the transport numbers of valproate and glutamate calculated at the 4-5$^{th}$ hours of current passage (0.4 mA) and at the 5-24th hours (0.1 mA).

From each individual cell, and at each sampling point, the ratio [extracted valproate/extracted glutamate] was obtained.

The means and standard deviations of these ratios are collected in Table III.

FIG. 6a shows the linear correlation between the extraction ratio (valproate/glutamate) and the valproate concentration in the sub-dermal solution.

FIG. 6b shows the linear correlation between the extracted ratio of the anions and their molar ratio (valproate/glutamate) in the sub-dermal solution.

TABLE II

Transport numbers (×10$^6$) of valproate and glutamate determined at each sampling period.

| Time (h) | [Valproate] = 21 μM | | [Valproate] = 35 μM | | [Valproate] = 70 μM | | [Valproate] = 104.5 μM | |
|---|---|---|---|---|---|---|---|---|
| | Valproate | Glutamate | Valproate | Glutamate | Valproate | Glutamate | Valproate | Glutamate |
| 0-1 | 1.20 ± 0.79 | 7.89 ± 4.51 | 2.23 ± 5.47 | 10.4 ± 5.47 | 3.56 ± 1.96 | 5.92 ± 3.03 | 8.04 ± 4.37 | 9.92 ± 4.20 |
| 1-2 | 3.38 ± 1.13 | 20.6 ± 7.92 | 7.60 ± 2.14 | 24.6 ± 5.83 | 12.4 ± 5.57 | 17.9 ± 6.88 | 21.0 ± 6.68 | 24.2 ± 4.79 |
| 2-3 | 5.26 ± 1.48 | 29.5 ± 7.38 | 10.8 ± 2.70 | 32.4 ± 5.71 | 18.0 ± 6.65 | 26.0 ± 6.32 | 29.5 ± 7.21 | 32.8 ± 3.60 |
| 3-4 | 6.15 ± 2.11 | 32.1 ± 5.77 | 13.5 ± 3.38 | 38.2 ± 2.84 | 22.9 ± 7.61 | 33.1 ± 6.80 | 35.6 ± 8.56 | 37.9 ± 4.98 |
| 4-5 | 7.48 ± 2.01 | 38.2 ± 5.19 | 14.8 ± 3.15 | 39.4 ± 3.28 | 24.7 ± 7.09 | 35.1 ± 5.52 | 40.2 ± 7.22 | 40.1 ± 5.16 |
| 5-24 | 10.9 ± 1.20 | 38.1 ± 6.24 | 22.0 ± 4.66 | 38.3 ± 4.24 | 42.9 ± 6.74 | 39.2 ± 6.45 | 61.0 ± 8.81 | 42.2 ± 6.22 |

TABLE III

Ratio of [valproate/glutamate] extraction fluxes as a function of time of sampling and as a function of subdermal valproate concentration. Subdermal glutamate concentration was always 60 μM. The current was 0.4 mA during the first 5 hours and 0.1 mA during the next 19 hours. Subdermal V/G is the ratio of valproate to glutamate concentrations in the donor, sub-dermal solution. Values are mean ± standard deviation.

| Time (h) | [Valproate] = 20.98 μM Subdermal V/G = 0.35 | [Valproate] = 34.96 μM Subdermal V/G = 0.58 | [Valproate] = 69.93 μM Subdermal V/G = 1.16 | [Valproate] = 104.5 μM Subdermal V/G = 1.74 |
|---|---|---|---|---|
| 0-1 | 0.17 ± 0.05 | 0.29 ± 0.08 | 0.59 ± 0.11 | 0.83 ± 0.25 |
| 1-2 | 0.17 ± 0.03 | 0.32 ± 0.09 | 0.68 ± 0.15 | 0.88 ± 0.25 |
| 2-3 | 0.18 ± 0.03 | 0.34 ± 0.09 | 0.68 ± 0.17 | 0.91 ± 0.23 |
| 3-4 | 0.19 ± 0.04 | 0.35 ± 0.09 | 0.68 ± 0.17 | 0.94 ± 0.21 |
| 4-5 | 0.20 ± 0.06 | 0.37 ± 0.08 | 0.70 ± 0.17 | 1.01 ± 0.19 |
| 5-24 | 0.29 ± 0.04 | 0.58 ± 0.15 | 1.10 ± 0.12 | 1.46 ± 0.22 |

To illustrate how this technique would work in practice, consider some practical situations using the information and relationships obtained from the experiments described above.

Consider a patient taking valproic acid, whose plasma glutamate concentration is 60 μM, and on whom a reverse iontophoretic procedure is performed.

Suppose that analysis of the extracted samples indicate that 741 pmoles of glutamate and 724 pmoles of valproate are extracted in 1 hour (4-5$^{th}$ hours of extraction).

The extracted ratio (valproate/glutamate) is 0.977.

Now this information could be used in different ways:

[a] Assume a therapeutic range for valproate of 3-10 mg/L (or 21 to 69 μM) of the free drug.

Such values correspond to molar ratios (valproate/glutamate) of 0.35 and 1.15 in the sub-dermal fluids.

According to our in vitro results (by substitution in the regression equation obtained at 5 hours, FIGS. 6a-b), an extraction ratio of 0.977 indicates that the valproate concentration systemically is 100 μM (FIG. 6a), i.e., the sub-dermal [valproate]/[glutamate] ratio is 1.67 (FIG. 6b).

We would conclude, therefore, that the valproate plasma levels of this patient were too high and out of the therapeutic range.

In fact, the values assumed for this hypothetical patient correspond to one of our in vitro experiments with a sub-dermal valproate concentration of 104.5 μM and a [valproate]/[glutamate] ratio of 1.74.

In other words, there is a good predictive value of the equations developed.

[b] For the molar sub-dermal ratios of 0.35 and 1.15 (low and high limits of the therapeutic window), iontophoresis extraction ratios of 0.21 and 0.68, respectively, can be deduced.

These are exactly the values predicted by the regression equation in FIG. 6b and we can therefore translate "real" plasma values, which delimit the therapeutic range, into extracted iontophoretic ratios.

We can now conclude that the plasma levels of valproate obtained from this patient are outside the therapeutic window: the extraction ratio of 0.977, falls well beyond the limits of 0.21 and 0.68.

This second approach can also be used for any situation in which the relative concentration of two markers (of clinical, therapeutic, toxic effect, etc.) is of relevance and interest.

It is important to note that the data of the example above correspond to one of the in vitro replicates in which the donor valproate concentration was held at 104.5 μM.

On the other hand, the regression equations used for the calculation were derived from many experiments performed with pig ear skin obtained from several different donors.

This supports our hypothesis that inter and intra-individual variability affects glutamate and valproate extraction in the same way.

It is further important to reiterate that FIGS. 6a-b demonstrate the determination of the constants K and K' necessary to calculate an absolute concentration of an analyte in the biological system from the extracted ratio of the analyte to the chosen internal standard.

In this example, the chosen analyte (A) is valproate, while the internal standard (B) is glutamate.

According to Equation 1, therefore, $$Q\text{val}/Q\text{glu} = K \cdot [\text{val}]/[\text{glu}]$$

K is the slope of the graph in FIG. 6b; that is, following a short (5-hour) period of iontophoresis at 0.5 mA/cm$^2$, K=0.57.

On the other hand, following a longer (19-hour) period of iontophoresis at 0.1 mA/cm$^2$, K=0.83.

Similarly, according to Equation 2, $$Q\text{val}/Q\text{glu} = K' \cdot [\text{val}]$$

K' is the slope of the graph in FIG. 6a and is equal to K divided by the fixed glutamate concentration (60 μM) in the biological system.

Following a short (5-hour) period of iontophoresis at 0.5 mA/cm$^2$, K'=0.0096

On the other hand, following a longer (19-hour) period of iontophoresis at 0.1 mA/cm$^2$, K'=0.0138.

It follows that, once the value of K' has been established for a particular pair of substances, and given that the concentration of the internal standard ([B]) in the biological system is constant, then Equation 2 can be used to determine the concentration of the analyte of interest ([A]) directly from the iontophoretic extraction ratio Qa/Qb.

Example 2

Figure 7:
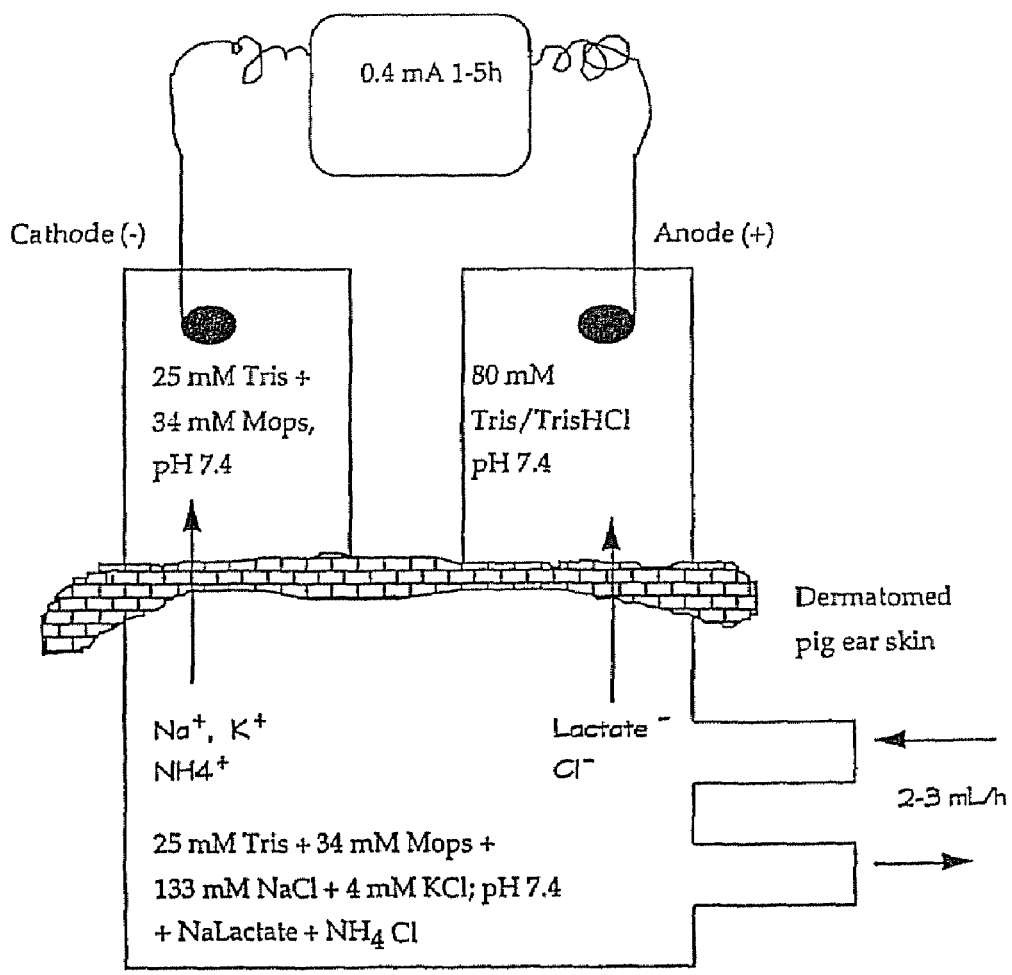
FIG. 7 represents a specifically-designed iontophoresis cell used for the in vitro experiments reported in Example 2.

Experiments were performed in specially-designed iontophoresis diffusion cells (Laboratory Glass Apparatus, Berkeley, Calif., USA) as represented in FIG. 7.

The sub-dermal (donor) solution was a pH 7.4 buffer (25 mM Tris+34 mM Mops+130 mM NaCl+4 mM KCl), in which potassium, sodium and chloride ions acted as the internal standards.

The two analytes of interest were lactate (negatively charged) and ammonium (positively charged).

In a first experiment, lactate and ammonium concentrations sub-dermally were 1.74 mM and 1.56 mM.

In a second experiment, lactate and ammonium concentrations were 0.73 mM and 0.78 mM.

The anodal and cathodal chambers contacted the outer surface of the skin and contained the receptor (collection) media, respectively, 80 mM Tris/TrisHCl and 25 mM Tris+34 mM Mops (both buffered to pH 7.4).

Dermatomed pig-ear skin was clamped between the two halves of the iontophoresis cell and each chamber was filled with the appropriate solution.

A schema of the experiment is shown in FIG. 7.

The sub-dermal chamber was filled with the "donor" solution which was perfused continuously at 2-3 mL/hour by means of a peristaltic pump.

A current of 0.4 mA (0.5 mA/cm$^2$) was passed for a total of 5 hours between the Ag/AgCl electrodes which were inserted into the anodal and cathodal chambers.

Every hour, the entire anode and cathode solutions were withdrawn and the chambers were refilled with fresh buffer.

All the samples were analyzed for lactate, ammonium, potassium, sodium and chloride.

As expected, the positively-charged ammonium, potassium and sodium cations were collected at the cathodal (negative) electrode, while the negatively-charged lactate and chloride anions were collected at the positive electrode (anode).

Table IV and FIGS. 8a-b show the extraction fluxes for these 5 species at the 3$^{rd}$ and 5$^{th}$ hours of the experiment.

Lactate and ammonium fluxes changed in proportion with their sub-dermal concentrations while the fluxes of potassium, chloride and sodium remained essentially constant.

TABLE IV

Extraction fluxes for Na+, K+ and ammonium+ at the cathode and for lactate− and chloride− at the anode.
Values are mean ± standard deviation.

| Analyte concentrations[a] | Time (h) | Ammonium (nmoles · $h^{-1}$ · $cm^{-2}$) | Lactate (nmoles · $h^{-1}$ · $cm^{-2}$) | K+ (nmoles · $h^{-1}$ · $cm^{-2}$) | Na+ (nmoles · $h^{-1}$ · $cm^{-2}$) | Cl− (nmoles · $h^{-1}$ · $cm^{-2}$) |
|---|---|---|---|---|---|---|
| [lactate] = 1.74 mM | 3 | 260 ± 17 | 113 ± 15 | 760 ± 90 | 12960 ± 1530 | 9430 ± 0 |
| [ammonium] = 1.56 mM | 5 | 275 ± 5 | 107 ± 13 | 780 ± 10 | 13790 ± 210 | 7850 ± 830 |
| [lactate] = 0.73 mM | 3 | 145 ± 18 | 45 ± 8 | 900 ± 27 | 13620 ± 218 | 5510 ± 1150 |
| [ammonium] = 0.78 mM | 5 | 140 ± 11 | 43 ± 10 | 820 ± 21 | 12460 ± 1540 | 7670 ± 1480 |

[a] Sub-dermal concentrations of K+, Na+ and Cl− were always 4 mM, 133 mM and 137 mM respectively.

Table V and FIGS. 9a-b present the transport numbers of the two analytes of interest (lactate and ammonium) and of the three internal standards (K+, Na+ and Cl−) considered.

For each individual cell and at each sampling time the following ratios of extracted ions were determined: [a] (ammonium/sodium), [b] (ammonium/potassium), [c] (lactate/chloride), [d] (lactate/sodium), [e] (lactate/potassium), and [f] (potassium/sodium).

The means and standard deviations of these ratios are shown in Table VI and FIGS. 10a-b.

These values in turn can be used to determine K and K' for each analyte/internal standard couple, as described in the preceding example.

The values of K are in Table VII below.

Values of K' can be obtained simply by dividing K by the appropriate concentration in the biological system of the applicable internal standard.

TABLE V

Deduced analyte and internal standard transport numbers (×100). Values are mean ± standard deviation.

| Analyte concentrations | Time (h) | Ammonium | Lactate | K+ | Na+ | Cl− |
|---|---|---|---|---|---|---|
| [lactate] = 1.74 mM | 3 | 1.36 ± 0.09 | 0.59 ± 0.08 | 3.99 ± 0.45 | 67.72 ± 7.98 | 57.68 ± 0.00 |
| [ammonium] = 1.56 mM | 5 | 1.44 ± 0.03 | 0.56 ± 0.07 | 4.06 ± 0.05 | 72.07 ± 1.07 | 50.69 ± 5.36 |
| [lactate] = 0.73 mM | 3 | 0.76 ± 0.09 | 0.24 ± 0.04 | 4.72 ± 1.40 | 71.17 ± 11.40 | 38.40 ± 8.04 |
| [ammonium] = 0.78 mM | 5 | 0.73 ± 0.06 | 0.23 ± 0.05 | 4.26 ± 1.08 | 65.14 ± 8.07 | 52.47 ± 10.12 |

TABLE VI

Extracted flux ratios (×$10^3$) of analytes and internal standards. Values are mean ± standard deviation.

| Analyte concentrations | Time (h) | $NH_4^+$/Na+ | $NH_4^+$/K+ | Lactate−/Na+ | Lactate−/K+ | Lactate−/Cl− | K+/Na+ |
|---|---|---|---|---|---|---|---|
| | | \multicolumn{6}{c}{Subdermal Ratio (·$10^3$)} | | | | | |
| | | 11.7 | 390 | 13.1 | 435 | 12.6 | 30 |
| [lactate] = 1.74 mM | 3 | 20 ± 1.1 | 342 ± 16 | 8.7 ± 0.1 | 149 ± 3.3 | 12 ± 1.6 | 59 ± 0.3 |
| [ammonium] = 1.56 mM | 5 | 20 ± 0.1 | 354 ± 11 | 7.8 ± 1.1 | 138 ± 15 | 14 ± 3.2 | 56 ± 1.6 |
| | | \multicolumn{6}{c}{Subdermal Ratio (·$10^3$)} | | | | | |
| | | 5.8 | 195 | 5.4 | 181 | 5.2 | 30 |
| [lactate] = 0.73 mM | 3 | 11 ± 1.0 | 166 ± 24 | 3.3 ± 0.6 | 52 ± 16 | 7.8 ± 1.0 | 66 ± 9.5 |
| [ammomium] = 0.78 mM | 5 | 11 ± 0.8 | 178 ± 29 | 3.5 ± 0.9 | 55 ± 19 | 6.0 ± 2.8 | 65 ± 8.7 |

TABLE VII

Values of K determined for each analyte/internal standard couple from the data in Table VI.

| Analyte concentrations | Time (h) | $NH_4^+$/Na+ | $NH_4^+$/K+ | Lactate−/Na+ | Lactate−/K+ | Lactate−/Cl− | K+/Na+ |
|---|---|---|---|---|---|---|---|
| | | \multicolumn{6}{c}{Subdermal Ratio (·$10^3$)} | | | | | |
| | | 11.7 | 390 | 13.1 | 435 | 12.6 | 30 |
| [lactate] = 1.74 mM | 3 | 1.71 ± 0.09 | 0.88 ± 0.04 | 0.66 ± 0.01 | 0.34 ± 0.01 | 0.95 ± 0.13 | 1.97 ± 0.01 |
| [ammonium] = 1.56 mM | 5 | 1.71 ± 0.01 | 0.91 ± 0.03 | 0.60 ± 0.08 | 0.32 ± 0.03 | 1.11 ± 0.25 | 1.87 ± 0.05 |

TABLE VII-continued

Values of K determined for each analyte/internal standard couple from the data in Table VI.

| Analyte concentrations | Time (h) | $NH_4^+/Na^+$ | $NH_4^+/K^+$ | Lactate$^-$/Na$^+$ | Lactate$^-$/K$^+$ | Lactate$^-$/Cl$^-$ | $K^+/Na^+$ |
|---|---|---|---|---|---|---|---|
| | | Subdermal Ratio ($\cdot 10^3$) | | | | | |
| | | 5.8 | 195 | 5.4 | 181 | 5.2 | 30 |
| [lactate] = 0.73 mM | 3 | 1.90 ± 0.09 | 0.85 ± 0.12 | 0.61 ± 0.11 | 0.29 ± 0.09 | 1.50 ± 0.19 | 2.20 ± 0.32 |
| [ammonium] = 0.78 mM | 5 | 1.90 ± 0.14 | 0.91 ± 0.15 | 0.65 ± 0.17 | 0.30 ± 0.10 | 1.15 ± 0.54 | 2.17 ± 0.29 |

It is clear that the data obtained in these experiments may be used as described in the first example to estimate whether the sub-dermal concentration of the analyte of interest falls within or outside an acceptable limit.

The use of more than one internal standard demonstrates the generality of the approach and offers a means to improve the precision, safety and accuracy of the method.

The consistency of the extraction ratio of internal standards acts as a further safety check, in that it permits the constancy of their sub-dermal levels (which is an assumed requirement) to be verified simply.

We also note that, despite the fact that lactate and Na$^+$ are collected at opposite electrodes, their extraction flux ratio is also a reflection of, and proportional to, the ratio of their sub-dermal concentrations.

This indicates that it is not always necessary to use, as an internal standard, a species which is extracted to the same electrode as the analyte of interest.

This may be important when assay methods interfere with one another, for example.

Lastly, the data in this example demonstrate that multiple analytes may be extracted and detected in a single reverse iontophoresis procedure and that the transport of each can be referenced to that of an appropriate "internal standard".

Example 3

Figure 11:
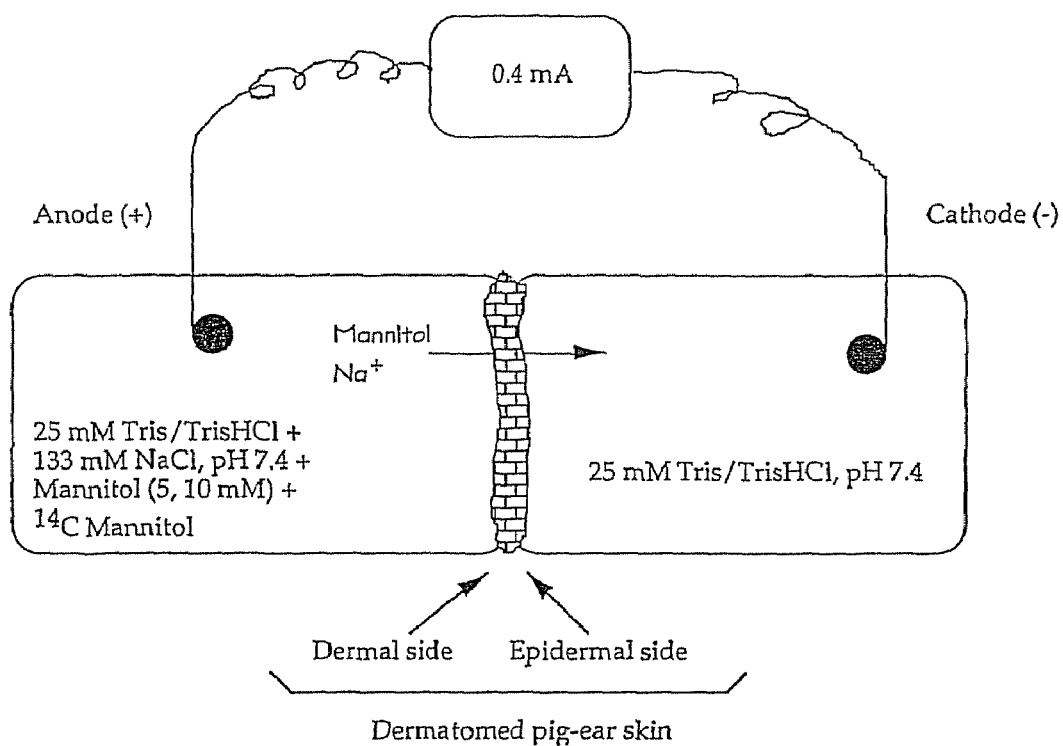
FIG. 11 represents a specifically-designed iontophoresis cell used for the in vitro experiments reported in Example 3.

Dermatomed pig-ear skin was clamped between the two halves of side-by-side diffusion cells (area=0.78 cm$^2$) as represented in FIG. 11.

The anode was placed in the sub-dermal, "donor" chamber, which contained a physiological pH 7.4 buffer (25 mM Tris/TrisHCl+133 mM NaCl) to which the analyte mannitol was added.

Mannitol is a non-metabolizable sugar with properties (including molecular weight and lipophilicity) very similar to glucose.

In a first experiment, mannitol concentration was 5 mM for the first three hours of experiment and was then increased to 10 mM for a subsequent period of three hours.

To facilitate the analytical chemistry, the donor solutions were spiked with $^{14}$C-labeled mannitol.

Sodium ion was the chosen internal standard.

The cathodal (collection) chamber, which contacted the outer surface of the skin contained a 25 mM Tris/TrisHCl buffer at pH 7.4.

A schema of the experiment is shown in FIG. 11.

A current of 0.4 mA (0.5 mA/cm$^2$) was passed between the Ag/AgCl electrodes for a total of 6 hours.

During the first 3-hour period, the entire content of the cathode solution was withdrawn every 60 minutes and the chamber was refilled with fresh buffer.

During the second 3-hour period, the 5 mM mannitol donor solution was replaced with 10 mM mannitol, and the cathodal chamber was then sampled every 30 minutes.

Mannitol and sodium ions in each sample were quantified by liquid scintillation counting and by an ion specific electrode, respectively.

Figure 12:
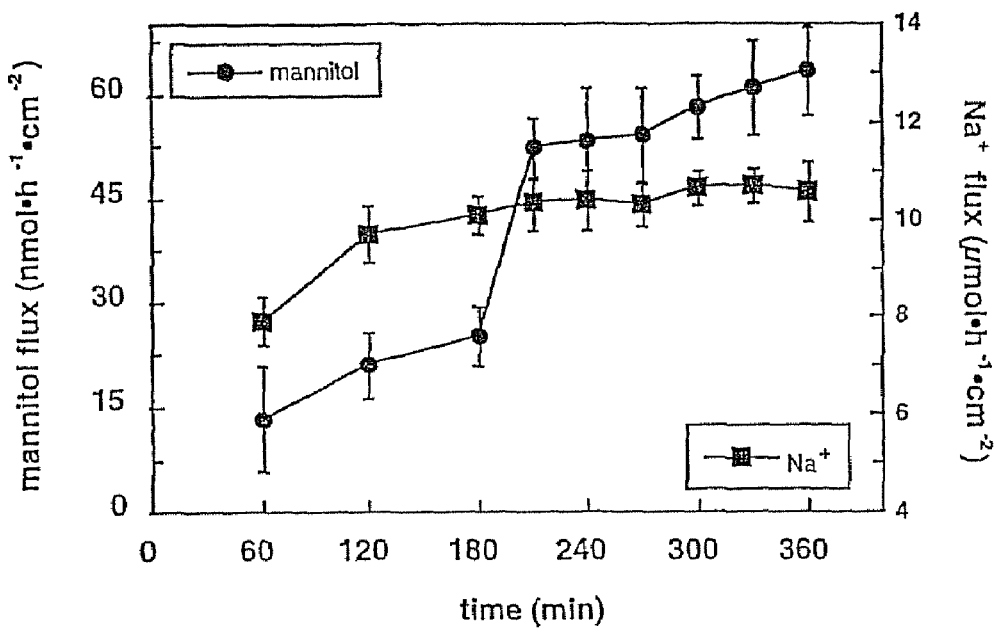
FIG. 12 represents the fluxes of mannitol and sodium over the six hours of the experiments reported in Example 3, first experiment.

FIG. 12 and Table VIII show the fluxes of mannitol and sodium over the six hours of experiment.

The data show that the mannitol flux changed abruptly when its concentration in the sub-dermal solution was increased from 5 to 10 mM.

On the other hand, the sodium flux reached a constant value that remained invariable over the entire course of the experiment.

Figure 13:
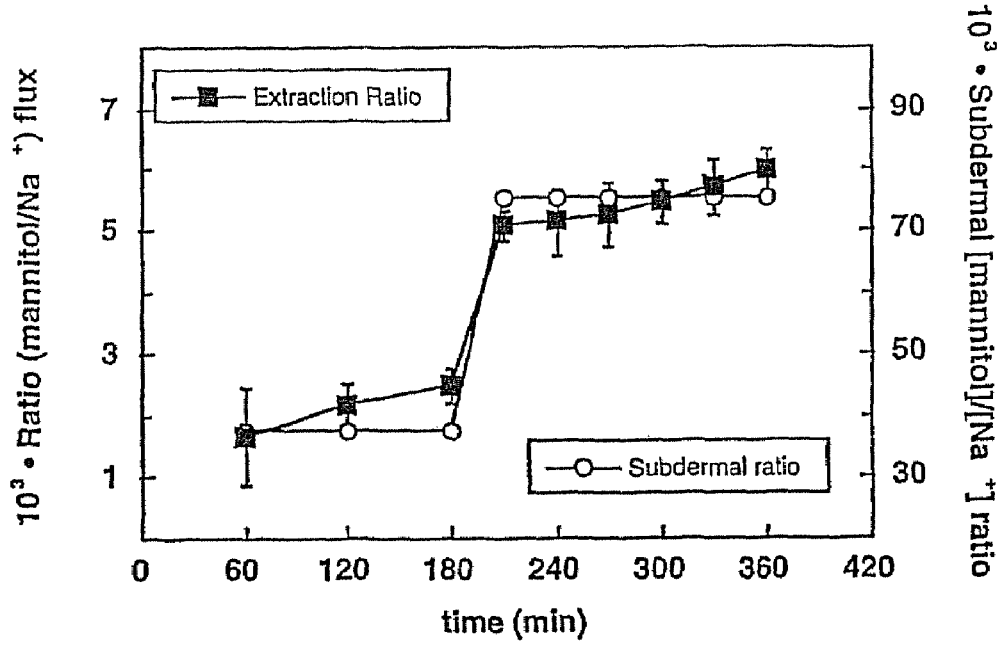
FIG. 13 represents the correlation between the iontophoretic extraction ratio of mannitol to sodium and their sub-dermal concentration ratio over the six hours of the experiments reported in Example 3, first experiment.

FIG. 13 and Table VIII show the correlation between the iontophoretic extraction ratio of mannitol to sodium and their sub-dermal concentration ratio over the six-hours period of the experiment.

TABLE VIII

Extraction fluxes and extracted flux ratios ($\times 10^3$) for mannitol and Na$^+$.
Values are mean ± standard deviation.

| Time (min) | [Mannitol] (mM) | Subdermal [mannitol/Na$^+$] ($\times 10^3$) ratio | Mannitol flux (nmol · h$^{-1}$ · cm$^{-2}$) | Sodium$^+$ flux (µmol · h$^{-1}$ · cm$^{-2}$) | Extracted (mannitol/Na$^+$) flux ($\times 10^3$) ratio |
|---|---|---|---|---|---|
| 60 | 5 | 37.6 | 13.3 ± 7.6 | 7.9 ± 0.5 | 1.7 ± 0.8 |
| 120 | | | 21.0 ± 4.7 | 9.7 ± 0.6 | 2.2 ± 0.3 |
| 180 | | | 25.2 ± 4.3 | 10.1 ± 0.4 | 2.5 ± 0.3 |
| 210 | 10 | 75.2 | 52.2 ± 4.4 | 10.3 ± 0.5 | 5.0 ± 0.2 |
| 240 | | | 53.2 ± 7.7 | 10.4 ± 0.6 | 5.1 ± 0.5 |
| 270 | | | 54.1 ± 6.8 | 10.3 ± 0.4 | 5.2 ± 0.5 |
| 300 | | | 58.1 ± 4.5 | 10.6 ± 0.3 | 5.5 ± 0.3 |

TABLE VIII-continued

Extraction fluxes and extracted flux ratios (×10³) for mannitol and Na⁺.
Values are mean ± standard deviation.

| Time (min) | [Mannitol] (mM) | Subdermal [mannitol/Na⁺] (×10³) ratio | Mannitol flux (nmol·h⁻¹·cm⁻²) | Sodium⁺ flux (μmol·h⁻¹·cm⁻²) | Extracted (mannitol/Na⁺) flux (×10³) ratio |
|---|---|---|---|---|---|
| 330 | | | 60.9 ± 6.8 | 10.7 ± 0.3 | 5.7 ± 0.4 |
| 360 | | | 63.2 ± 6.2 | 10.5 ± 0.6 | 6.0 ± 0.3 |

In a second experiment, performed under identical conditions to the first (see FIG. 11), mannitol concentration was 5 mM for the first three hours of experiment, it was then reduced to 3 mM for a subsequent period of one hour and then increased to 10 mM for a subsequent period of one hour.

Sodium ion was again the chosen internal standard.

A current of 0.4 mA (0.5 mA/cm²) was passed between the Ag/AgCl electrodes for a total of 5 hours.

During the first 3-hour period, the entire content of the cathode solution was withdrawn every 60 minutes and the chamber was refilled with fresh buffer.

During the second 1-hour period, the 5 mM mannitol donor solution was replaced with 3 mM mannitol, and the cathodal chamber was then sampled every 30 minutes.

During the third 1-hour period, the 3 mM mannitol donor solution was replaced with 10 mM mannitol, and the cathodal chamber was then sampled every 30 minutes.

Mannitol and sodium ions in each sample were again quantified by liquid scintillation counting and by an ion specific electrode, respectively.

FIGS. 14a-b and Table IX show the fluxes of mannitol and sodium and also the (mannitol/sodium) extraction flux ratio over the 5 hours of experiment.

TABLE IX

Extraction fluxes and extracted flux ratios (×10³) for mannitol and Na⁺.
Values are mean ± standard deviation.

| Time (min) | [Mannitol] (mM) | Subdermal [mannitol/Na⁺] (×10³) ratio | Mannitol flux (nmol·h⁻¹·cm⁻²) | Sodium⁺ flux (μmol·h⁻¹·cm⁻²) | Extracted (mannitol/Na⁺) flux (×10³) ratio |
|---|---|---|---|---|---|
| 60 | 5 | 37.6 | 13.5 ± 4.1 | 8.8 ± 0.7 | 1.52 ± 0.4 |
| 120 | | | 25.8 ± 4.8 | 10.2 ± 0.7 | 2.5 ± 0.3 |
| 180 | | | 27.8 ± 4.4 | 10.4 ± 0.7 | 2.7 ± 0.3 |
| 210 | 3 | 22.5 | 16.6 ± 3.2 | 10.9 ± 0.7 | 1.5 ± 0.2 |
| 240 | | | 14.1 ± 2.8 | 9.7 ± 0.5 | 1.5 ± 0.5 |
| 270 | 10 | 75.2 | 49.6 ± 8.4 | 9.4 ± 0.6 | 5.2 ± 0.5 |
| 300 | | | 48.1 ± 8.7 | 9.3 ± 0.4 | 5.2 ± 0.7 |

The data show that the mannitol flux nearly halved when its concentration in the sub-dermal solution was decreased from 5 to 3 mM and then increased abruptly when the sub-dermal solution was increased from 3 to 10 mM.

On the other hand, the sodium flux reached a constant value that remained invariable over the entire course of the experiment.

FIGS. 15a-b show the correlation between the iontophoretic extraction ratio of mannitol to sodium and [a] the mannitol sub-dermal concentration, and [b] the sub-dermal concentration ratio (mannitol/sodium) over the 5-hour period of the experiment.

The two experiments in this example clearly show that the reverse iontophoretic extraction of a neutral molecule (mannitol) by electroosmosis can be "calibrated" by the use of an ionic internal standard (Na⁺) which moves across the skin by electromigration.

The molecular similarity between mannitol and glucose implies that the same approach can be used for glucose monitoring, as will demonstrated in a subsequent example.

To illustrate how this technique would work in practice, consider some practical situations using the information and relationships obtained from the experiments described above.

Consider a hypothetical patient, whose NaCl concentration in plasma is 133 mM, on whom a reverse iontophoretic procedure is performed.

Suppose that analysis of the extracted samples indicates that 14.26 nmoles of mannitol and 10.14 μmoles of sodium are extracted across 1 cm² of skin in 1 hour.

The extracted ratio (mannitol/sodium) is $1.4 \times 10^{-3}$.

Now this information could be used in different ways:

[a] Assume, in this hypothetical patient, that the "normal" concentration range of mannitol is 80-100 mg/dL (or 4.4 to 5.5 mM).

Such values correspond to molar ratios (mannitol/sodium) of $33 \times 10^{-3}$ and $41 \times 10^{-3}$ in the sub-dermal fluids, assuming a constant sodium concentration of 133 mM.

According to our in vitro results (by substitution in the regression equation of FIG. 15a), an extraction ratio of $1.4 \times 10^{-3}$ indicates that the mannitol concentration systemically is 2.8 mM, i.e., the sub-dermal [mannitol]/[sodium] ratio is $20.7 \times 10^{-3}$ (FIG. 15b).

We would conclude, therefore, that the mannitol plasma levels of this patient were too low.

In fact, the values assumed for this hypothetical patient correspond to one of our in vitro experiments with a sub-dermal mannitol concentration of 3 mM and a [mannitol]/[sodium] ratio of $22.5 \times 10^{-3}$.

In other words, there is a good predictive value of the equations developed.

[b] For the molar sub-dermal ratios of $33\times10^{-3}$ and $41\times10^{-3}$ (low and high limits of the "hypothetical" normal range of mannitol), iontophoresis extraction ratios of $2.26\times10^{-3}$ and $2.82\times10^{-3}$, respectively, can be deduced.

These are exactly the values predicted by the regression equation in FIG. 15b and we can therefore translate "real" plasma values, which delimit the acceptable range, into extracted iontophoretic ratios.

We can now conclude that the plasma levels of mannitol obtained from this patient are outside the normal range: the extraction ratio of $1.4\times10^{-3}$, falls well beyond the limits of $2.26\times10^{-3}$ and $2.82\times10^{-3}$.

It is further important to reiterate that FIGS. 15a-b demonstrate the determination of the constants K and K' necessary to calculate an absolute concentration of an analyte in the biological system from the extracted ratio of the analyte to the chosen internal standard.

In this example, the chosen analyte (A) is mannitol, while the internal standard (B) is $Na^+$.

According to Equation 1, therefore, $Q\text{mann}/Q\text{Na}^+ = K \cdot [\text{mann}]/[\text{Na}^+]$ K can be read from the slope of the graph in FIG. 15b; that is, following periods of iontophoresis of between 3 and 5 hours at $0.5$ mA/cm$^2$, K=0.07.

Similarly, according to Equation 2, $Q\text{mann}/Q\text{Na}^+ = K' \cdot [\text{mann}]$ K' can be read from the slope of the graph in FIG. 15a and is equal to K divided by the fixed $Na^+$ concentration (133 mM) in the biological system.

Following periods of iontophoresis of between 3 and 5 hours at $0.5$ mA/cm$^2$, K'=$0.525\times10^{-3}$.

It follows that, once the value of K' has been established for a particular pair of substances, and given that the concentration of the internal standard ([B]) in the biological system is constant, then Equation 2 can be used to determine the concentration of the analyte of interest ([A]) directly from the iontophoretic extraction ratio Qa/Qb.

Example 4

Dermatomed pig-ear skin was clamped between the two halves of side-by-side diffusion cells (area=$0.78$ cm$^2$).

The anode was placed in the sub-dermal, "donor" chamber, which contained a physiological pH 7.4 buffer (25 mM Tris/TrisHCl+4 mM KCl).

The analyte of interest was mannitol and sodium ion was the chosen internal standard.

Both the concentration of the analyte of interest and the internal standard were modified during the experiment.

Sodium and mannitol concentrations were 133 and 5 mM, respectively, for the first three hours.

Then, sodium and mannitol concentrations were changed to 125 and 10 mM, respectively, for a subsequent period of one hour.

Then, sodium and mannitol concentrations were changed to 145 and 3 mM, respectively, for a subsequent period of one hour.

Finally, sodium and mannitol concentrations were changed to 133 and 5 mM, respectively, for the last hour of the experiment.

The range of sodium concentrations chosen corresponds to that which can occur normally in human subjects.

In other words, there will almost always be some slight variation in the concentration of an internal standard in the biological system.

The objective of this experiment was to test, therefore, whether such typical variability would impact significantly on the results deduced from a reverse iontophoresis procedure based on the invention disclosed.

To facilitate the analytical chemistry, the donor solutions were spiked with $^{14}C$-labeled mannitol.

The cathodal (collection) chamber, which contacted the outer surface of the skin, contained a 25 mM Tris/TrisHCl buffer at pH 7.4.

Figure 16:
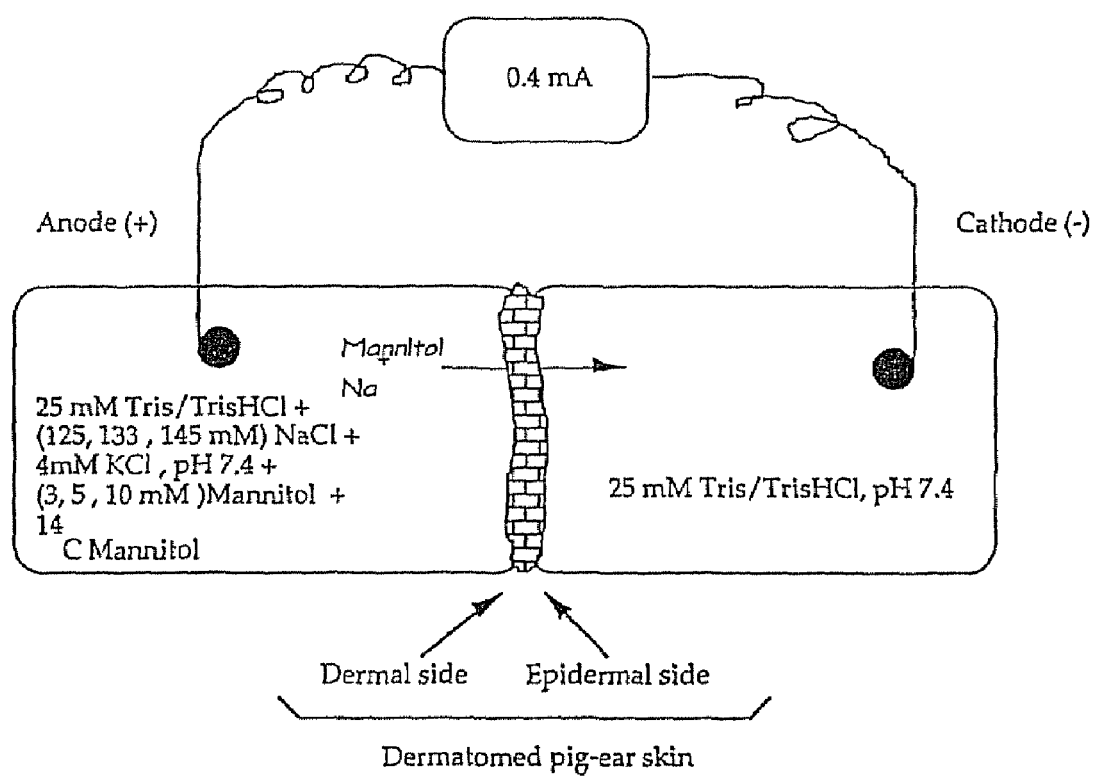
FIG. 16 represents a specifically-designed iontophoresis cell used for the in vitro experiments reported in Example 4.
Figure 17:
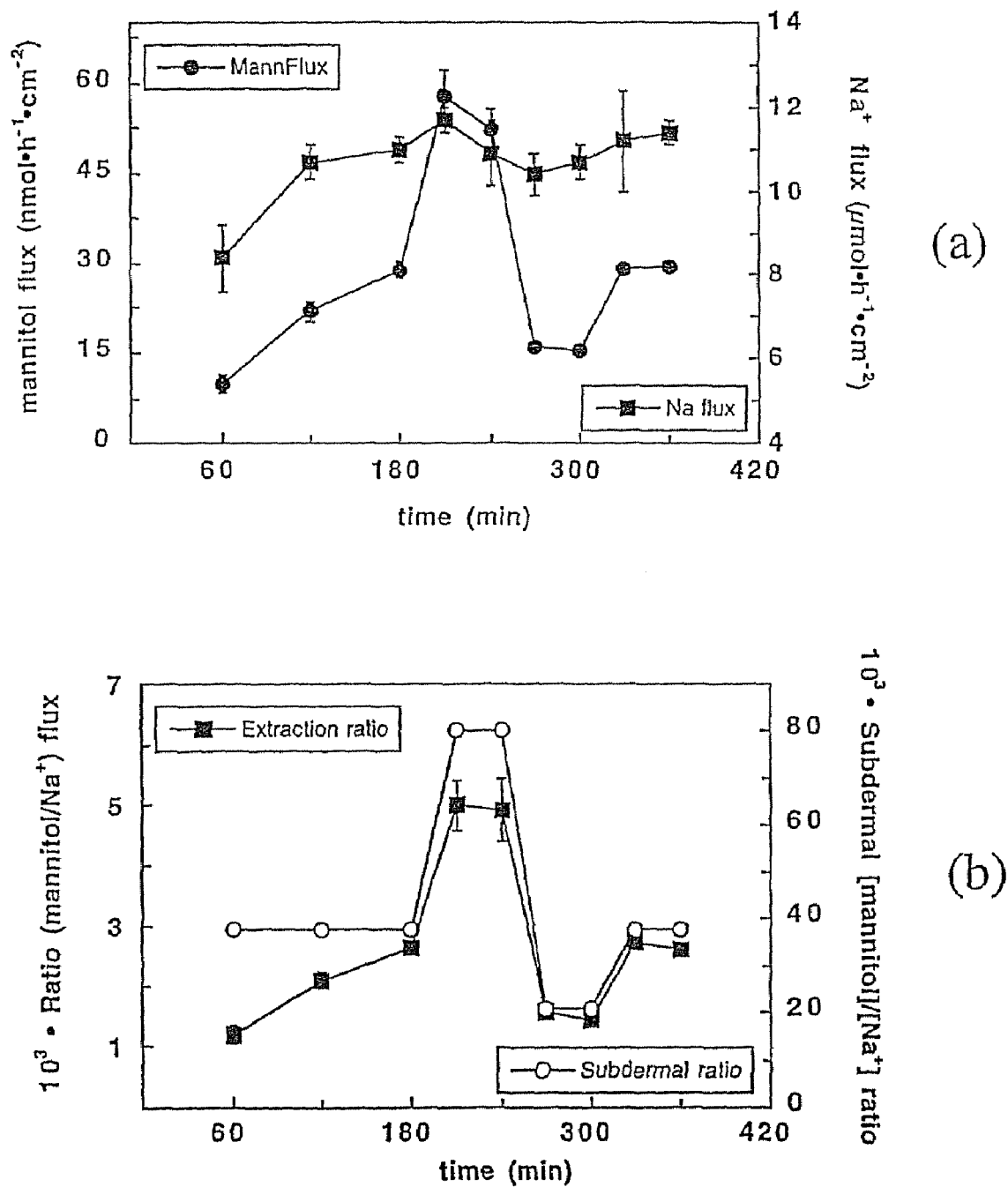
FIGS. 17a-b show the fluxes of mannitol and sodium and the (mannitol/sodium) extraction flux ratio over the 6 hours of the experiments reported in Example 4.

A schema of the experiment is shown in FIG. 16.

A current of 0.4 mA (0.5 mA/cm$^2$) was passed between the Ag/AgCl electrodes for a total of 6 hours.

During the first 3-hour period, the entire content of the cathode solution was withdrawn every 60 minutes and the chamber was refilled with fresh buffer.

During the second 1-hour period, the 5 mM mannitol/133 mM NaCl donor solution was replaced with 10 mM mannitol/125 mM NaCl, and the cathodal chamber was then sampled every 30 minutes.

During the third 1-hour period, the donor solution was replaced with 3 mM mannitol/145 mM NaCl, and the cathodal chamber was then sampled every 30 minutes.

During the final 1-hour period, the donor solution was replaced with 5 mM mannitol/133 mM NaCl, and the cathodal chamber was then sampled every 30 minutes.

Mannitol and sodium ions in each sample were quantified by liquid scintillation counting and by an ion specific electrode, respectively.

FIGS. 17a-b and Table X show the extraction fluxes and also the (mannitol/sodium) extraction flux ratio over the 6 hours of experiment.

TABLE X

Extraction fluxes and extracted flux ratios ($\times10^3$) for mannitol and $Na^+$.
Values are mean ± standard deviation.

| Time (min) | [Mannitol]/[Na$^+$] (mM) | Subdermal [mannitol/Na$^+$] ($\times10^3$) ratio | Mannitol flux (nmol·h$^{-1}$·cm$^{-2}$) | Sodium$^+$ flux (μmol·h$^{-1}$·cm$^{-2}$) | Extracted (mannitol/Na$^+$) flux ($\times10^3$) ratio |
|---|---|---|---|---|---|
| 60 | 5/133 | 37.6 | 9.7 ± 1.5 | 8.4 ± 0.8 | 1.2 ± 0.2 |
| 120 | | | 22.0 ± 1.6 | 10.7 ± 0.4 | 2.1 ± 0.1 |
| 180 | | | 28.8 ± 1.3 | 11.0 ± 0.3 | 2.6 ± 0.1 |
| 240 | 10/125 | 80 | 57.7 ± 4.2 | 11.7 ± 0.3 | 5.0 ± 0.4 |
| 240 | | | 52.2 ± 3.3 | 10.9 ± 0.8 | 4.9 ± 0.5 |
| 270 | 3/145 | 20.7 | 15.9 ± 0.7 | 10.4 ± 0.5 | 1.6 ± 0.1 |
| 300 | | | 15.3 ± 0.7 | 10.7 ± 0.4 | 1.4 ± 0.1 |

TABLE X-continued

Extraction fluxes and extracted flux ratios (×10³) for mannitol and Na⁺.
Values are mean ± standard deviation.

| Time (min) | [Mannitol]/[Na⁺] (mM) | Subdermal [mannitol/Na⁺] (×10³) ratio | Mannitol flux (nmol·h⁻¹·cm⁻²) | Sodium⁺ flux (μmol·h⁻¹·cm⁻²) | Extracted (mannitol/Na⁺) flux (×10³) ratio |
|---|---|---|---|---|---|
| 330 | 5/133 | 37.6 | 29.0 ± 0.8 | 11.2 ± 1.2 | 2.7 ± 0.1 |
| 360 | | | 29.3 ± 0.6 | 11.4 ± 0.3 | 2.6 ± 0.1 |

Figure 18:
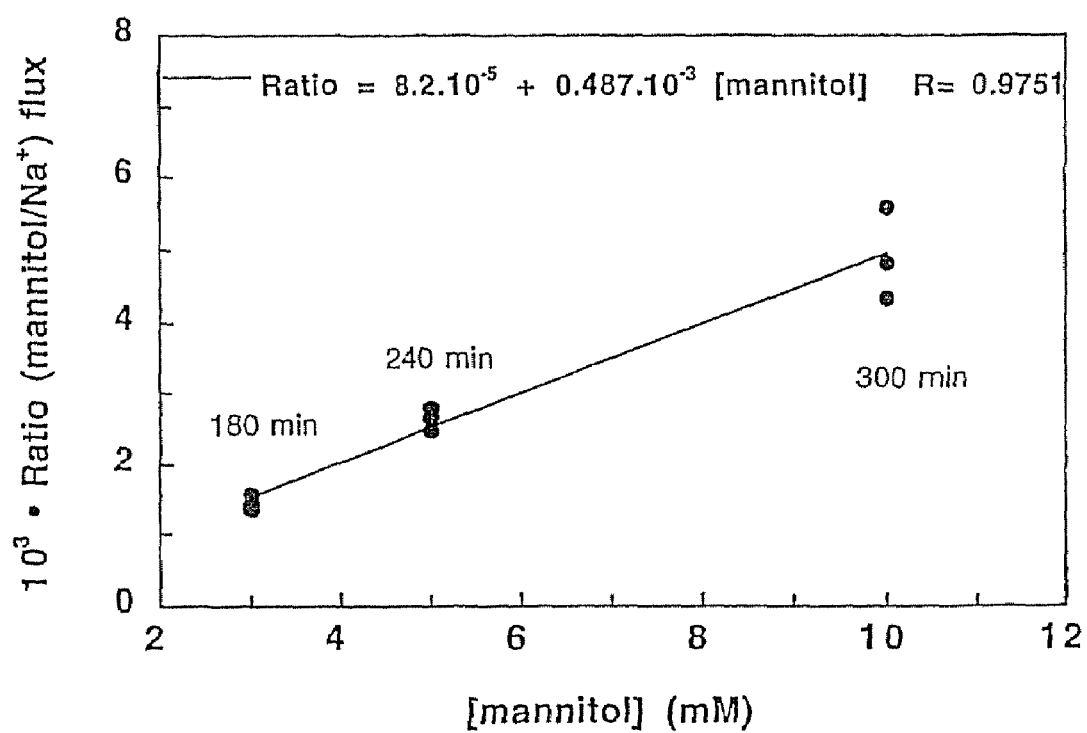
FIG. 18 shows the correlation between the iontophoretic extraction ratio of mannitol to sodium and the mannitol sub-dermal concentration over the 6-hour period of the experiments reported in Example 4.

FIG. 18 shows the correlation between the iontophoretic extraction ratio of mannitol to sodium and the mannitol subdermal concentration over the 6-hour period of the experiment.

This example clearly shows that the reverse iontophoretic extraction of a neutral molecule (mannitol) by electroosmosis can be "calibrated" by the use of an ionic internal standard (Na⁺) which moves across the skin by electromigration.

The molecular similarity between mannitol and glucose implies that the same observations made here would be equally applicable for glucose monitoring, as will demonstrated in a subsequent example.

Furthermore, this example shows that the method is not undermined by typical variations in the concentration (in the biological system) of the internal standard, in this case sodium ions.

To illustrate how this technique would work in practice, consider some practical situations using the information and relationships obtained from the experiments described above.

Consider a hypothetical patient on whom a reverse iontophoretic procedure is performed.

Suppose that analysis of the extracted samples indicates that 58 nmoles of mannitol and 11.7 μmoles of sodium are extracted across 1 cm² of skin in 1 hour.

The extracted ratio (mannitol/sodium) is $4.97 \times 10^{-3}$.

Now this information could be used as follows:

[a] Assume, in this hypothetical patient, that the "normal" range for mannitol of 80-100 mg/dL (or 4.4 to 5.5 mM) and that the patient's sodium concentration may vary in the interval 125-145 mM.

Thus, in this case, constant levels of the internal standard are not assumed.

According to our in vitro results (by substitution in the regression equation of FIG. 18a) an extraction ratio of $4.97 \times 10^{-3}$ indicates that the mannitol concentration systemically is 10 mM, i.e., we would conclude, therefore, that the mannitol plasma levels of this patient were too high In fact, the values assumed for this hypothetical patient correspond to one of our in vitro experiments with a sub-dermal mannitol concentration of 10 mM and a [mannitol]/[sodium] ratio of $80 \times 10^{-3}$.

In other words, there is a good predictive value of the equations developed.

[b] For the low and high limits (4.4 to 5.5 mM) of the "hypothetical" normal range of mannitol, iontophoresis extraction ratios of $2.2 \times 10^{-3}$ and $2.8 \times 10^{-3}$, respectively, can be deduced.

These are exactly the values predicted by the regression equation in FIG. 18 and we can therefore translate "real" plasma values, which delimit the acceptable range, into extracted iontophoretic ratios.

We can now conclude that the plasma levels of mannitol obtained from this patient are outside the normal range: the extraction ratio of $4.97 \times 10^{-3}$ falls well beyond the limits of $2.2 \times 10^{-3}$ and $2.8 \times 10^{-3}$.

It should be recalled that FIG. 18 can be used to demonstrate the determination of the constant K' necessary to calculate an absolute concentration of an analyte in the biological system from the extracted ratio of the analyte to the chosen internal standard.

This procedure was described using the data in the preceding example and the regressions in FIG. 15a.

Interestingly, the slope of the regression in FIG. 18 is very close to those in FIG. 15a.

From FIG. 15a, K' is deduced to be $0.525 \times 10^{-3}$; from FIG. 18, $K' = 0.487 \times 10^{-3}$.

In other words, we derive essentially the same calibration parameter from the experiments in this example in which the concentration of the internal standard was allowed to vary over an interval which may be observed in a typical biological system.

We conclude, therefore, that the approach is robust.

Example 5

Dermatomed pig-ear skin was clamped between the two halves of side-by-side diffusion cells (area=0.78 cm²).

The anode was placed in the sub-dermal, "donor" chamber, which contained a physiological pH 7.4 buffer (25 mM Tris/TrisHCl+133 mM NaCl) to which the analyte glucose was added at a concentration of 10 mM.

To facilitate the analytical chemistry, the donor solutions were spiked with tritiated glucose.

Sodium ion was the chosen internal standard.

The cathodal (collection) chamber, which contacted the outer surface of the skin, contained a 25 mM Tris/TrisHCl buffer at pH 7.4.

The experimental design was identical to that in FIG. 11, with the exception that glucose spiked with tritiated glucose replaced mannitol spiked with ¹⁴C-labeled mannitol.

A current of 0.4 mA (0.5 mA/cm²) was passed between the Ag/AgCl electrodes for a total of 6 hours.

During this period, the entire content of the cathode solution was withdrawn every 60 minutes and the chamber was refilled with fresh buffer.

Glucose and sodium ions in each sample were quantified by liquid scintillation counting and by an ion specific electrode, respectively.

Figure 19:
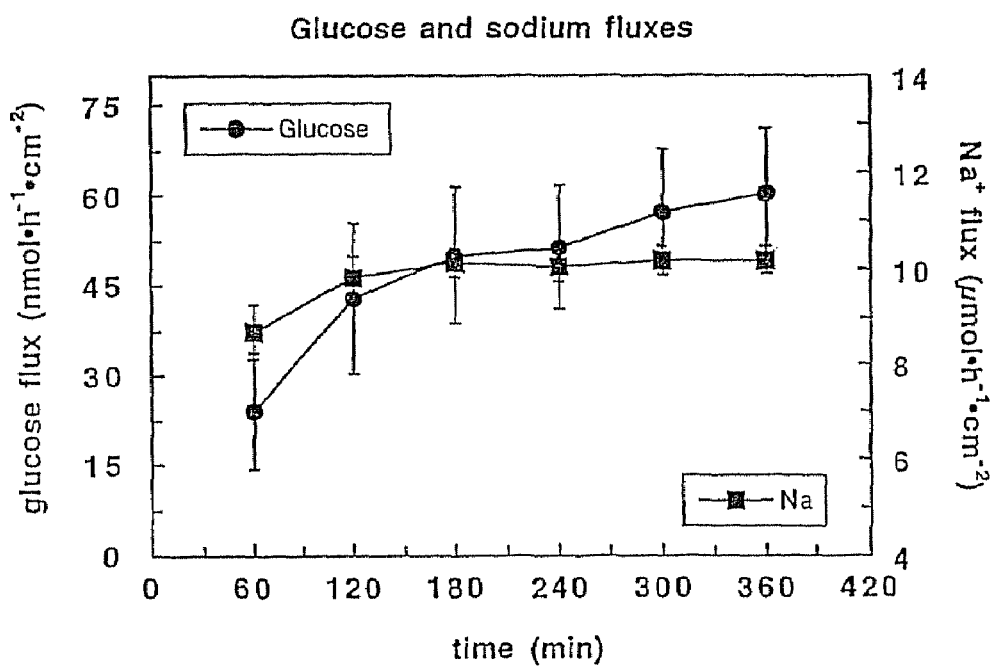
FIG. 19 shows the fluxes of glucose and sodium over the 6 hours of the experiment reported in Example 5.
Figure 20:
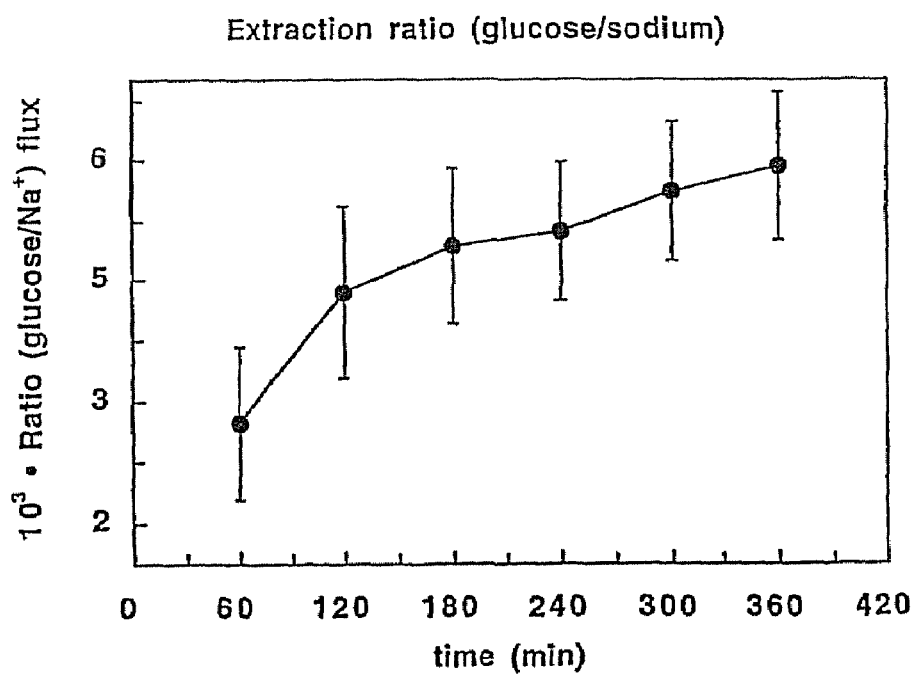
FIG. 20 shows the (glucose/sodium) extraction flux ratio over the 6 hours of the experiment reported in Example 5.
Figure 21:
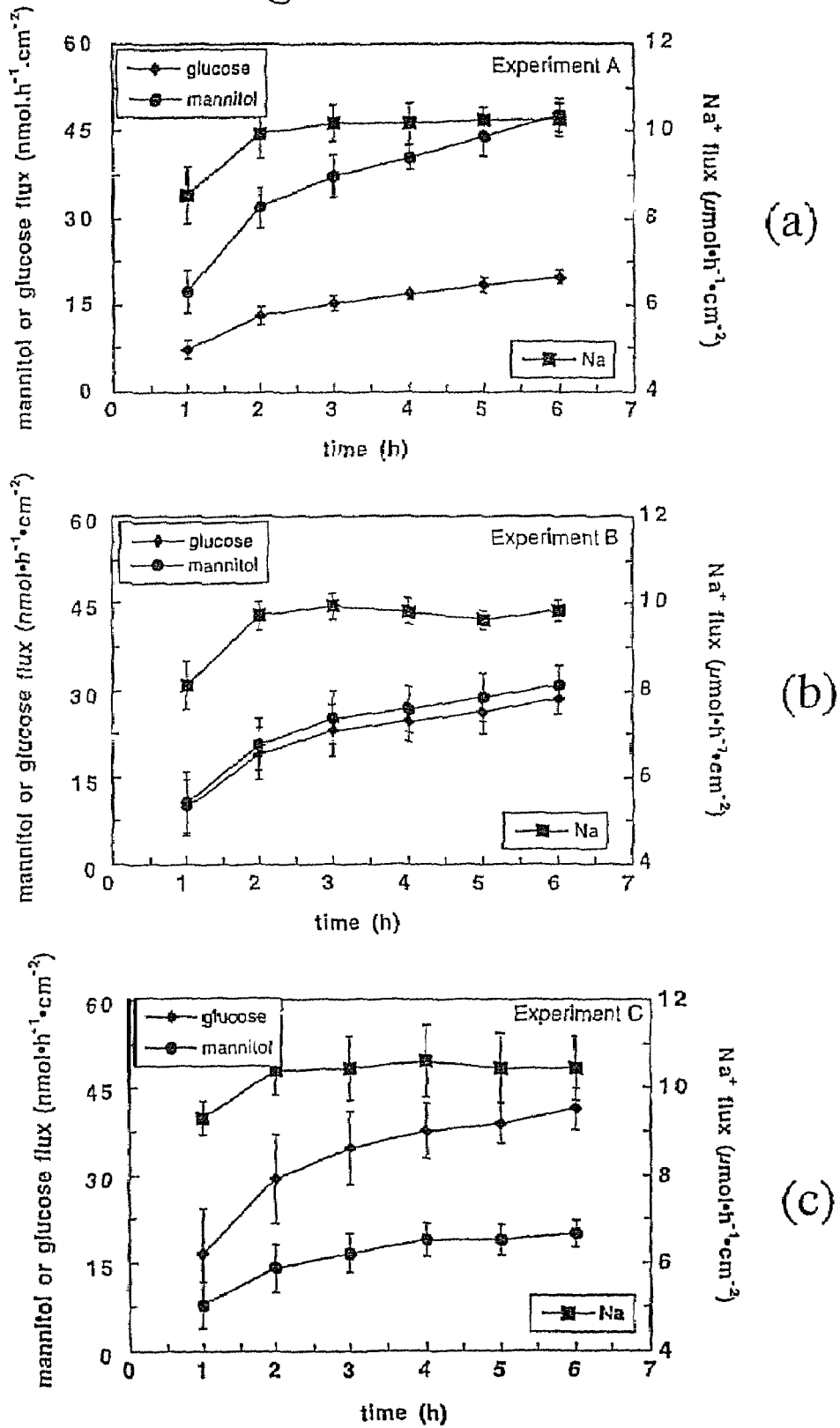
FIG. 21a-c show the fluxes of glucose, mannitol and sodium during the 6-hour periods of Experiments A, B and C, respectively, reported in Example 6.
Figure 22:
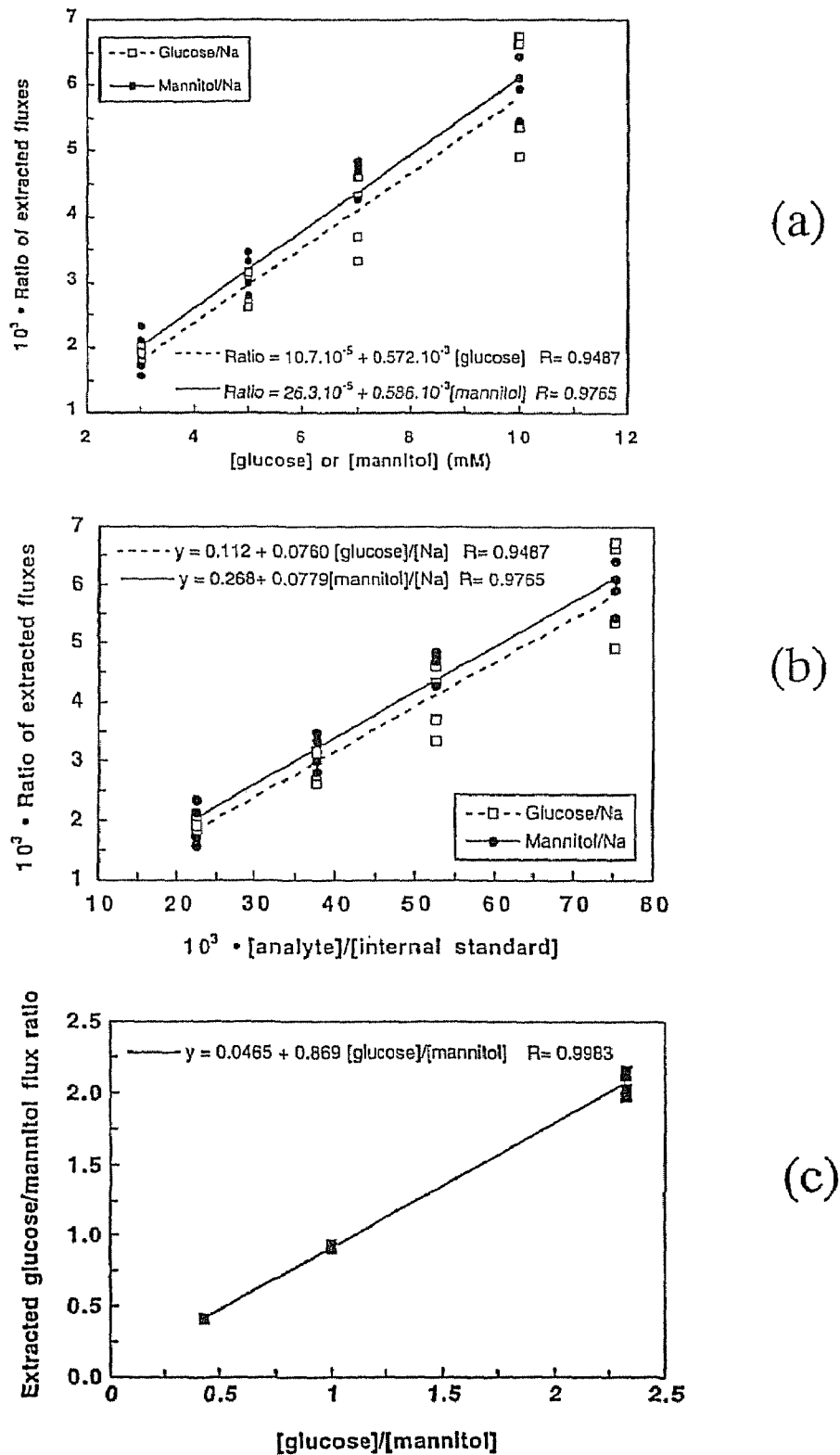
FIG. 22a shows the correlation between (a) the iontophoretic extraction ratio of glucose to sodium and the glucose sub-dermal concentration, and (b) the iontophoretic extraction ratio of mannitol to sodium and the mannitol sub-dermal concentration, following 6 hours iontophoresis at 0.5 mA/cm², as reported in Example 6.
FIG. 22b shows the correlation between (a) the iontophoretic extraction ratio of glucose to sodium and the sub-dermal concentration ratio (glucose/sodium), and (b) the iontophoretic extraction ratio of mannitol to sodium and the sub-dermal concentration ratio (mannitol/sodium), following 6 hours iontophoresis at 0.5 mA/cm², as reported in Example 6.
FIG. 22c shows the correlation between the iontophoretic extraction ratio of glucose to mannitol and the sub-dermal concentration ratio (glucose/mannitol), following 6 hours iontophoresis at 0.5 mA/cm², as reported in Example 6.

FIGS. 19 and 20 and Table XI show the fluxes of glucose and sodium and also the (glucose/sodium) extraction flux ratio over the 6 hours of experiment.

TABLE XI

Extraction fluxes and extracted flux ratios (×10³) for glucose and Na⁺.
Values are mean ± standard deviation.

| Time (min) | [Glucose] (mM) | Subdermal [glucose/Na⁺] (×10³) ratio | Glucose flux (nmol·h⁻¹·cm⁻²) | Sodium⁺ flux (μmol·h⁻¹·cm⁻²) | Extracted (glucose/Na⁺) flux (×10³) ratio |
|---|---|---|---|---|---|
| 60  | 10 | 75.2 | 24.1 ± 9.8  | 8.7 ± 0.6  | 2.7 ± 0.9 |
| 120 |    |      | 43.0 ± 12.6 | 9.8 ± 0.4  | 4.4 ± 1.1 |
| 180 |    |      | 50.1 ± 11.4 | 10.1 ± 0.3 | 4.9 ± 1.0 |
| 240 |    |      | 51.5 ± 10.4 | 10.0 ± 0.3 | 5.1 ± 0.9 |
| 300 |    |      | 57.3 ± 10.6 | 10.2 ± 0.3 | 5.6 ± 0.9 |
| 360 |    |      | 60.5 ± 10.8 | 10.2 ± 0.3 | 5.9 ± 0.9 |

The data are remarkably similar to those obtained in the essentially identical experiment described in Example 3 in which mannitol was used instead of glucose.

The comparison is made with the data in the lower half of Table VIII, and with the graphical results in FIGS. 12 and 13 at times after 180 minutes.

This example clearly shows that the reverse iontophoretic extraction of a neutral molecule (glucose) by electroosmosis can be "calibrated" by the use of an ionic internal standard (Na⁺) which moves across the skin by electromigration.

Further, the results confirm that mannitol is a good model for glucose and that the method is applicable, therefore, to noninvasive glucose monitoring applications.

Example 6

Dermatomed pig-ear skin was clamped between the two halves of side-by-side diffusion cells (area=0.78 cm²).

The anode was placed in the sub-dermal, "donor" chamber, which contained a physiological pH 7.4 buffer (25 mM Tris/TrisHCl+133 mM NaCl) to which the analytes glucose and mannitol were both added, in separate experiments, each of 6 hours duration, at the following concentrations:

Glucose, 3 mM; mannitol, 7 mM—Experiment A
Glucose, 5 mM; mannitol, 5 mM—Experiment B
Glucose, 7 mM, mannitol, 3 mM—Experiment C To facilitate the analytical chemistry, the donor solutions were spiked with tritiated glucose and $^{14}$C-labeled mannitol.

Sodium ion was the chosen internal standard.

The cathodal (collection) chamber, which contacted the outer surface of the skin, contained a 25 mM Tris/TrisHCl buffer at pH 7.4.

The experimental design was identical to that in FIG. 11, with the exception that both tritiated glucose and $^{14}$C-labeled mannitol were present in the 'donor' anode chamber.

A current of 0.4 mA (0.5 mA/cm²) was passed between the Ag/AgCl electrodes for a total of 6 hours.

During this period, the entire content of the cathode solution was withdrawn every 60 minutes and the chamber was refilled with fresh buffer.

Glucose and mannitol in each sample were quantified by liquid scintillation counting; sodium was quantified using an ion specific electrode.

FIGS. 21a-c show the fluxes of glucose, mannitol and sodium during the 6-hour periods of Experiments A, B and C, respectively.

The data show that glucose and mannitol fluxes responded proportionately to their sub-dermal concentrations.

The sodium flux was constant, and had the same absolute value, in each of Experiments A, B and C.

Tables XII, XIII and XIV show the (glucose/sodium), (mannitol/sodium) and (glucose/mannitol) extracted flux ratios, in Experiments A, B and C, respectively, over the 6-hour period of these measurements.

TABLE XII

Extracted flux ratios when the subdermal concentrations of glucose (G) and mannitol (M) were 3 mM and 7 mM, respectively (Experiment A, Example 6). Values are mean ± standard deviation.

| Time (minutes) | Subdermal concentration ratios | | | Extracted flux ratios | | |
|---|---|---|---|---|---|---|
|  | (10³×) [G]/[Na⁺] | (10³×) [M]/[Na⁺] | [glucose]/[mannitol] | (10³×) G/Na⁺ | (10³×) M/Na⁺ | G/M |
| 60  | 22.5 | 52.6 | 0.43 | 0.85 ± 0.13 | 2.01 ± 0.33 | 0.42 ± 0.01 |
| 120 |      |      |      | 1.32 ± 0.09 | 3.21 ± 0.21 | 0.41 ± 0.01 |
| 180 |      |      |      | 1.50 ± 0.10 | 3.64 ± 0.31 | 0.41 ± 0.01 |
| 240 |      |      |      | 1.65 ± 0.09 | 3.98 ± 0.24 | 0.41 ± 0.00 |
| 300 |      |      |      | 1.79 ± 0.15 | 4.29 ± 0.40 | 0.42 ± 0.01 |
| 360 |      |      |      | 1.92 ± 0.10 | 4.65 ± 0.26 | 0.41 ± 0.00 |

TABLE XIII

Extracted flux ratios when the subdermal concentrations of glucose (G) and mannitol (M) were 5 mM and 5 mM, respectively (Experiment B, Example 6). Values are mean ± standard deviation.

| Time | Subdermal concentration ratios | | | Extracted flux ratios | | |
|---|---|---|---|---|---|---|
| (minutes) | $(10^3 \times)$ [G]/[Na$^+$] | $(10^3 \times)$ [M]/[Na$^+$] | [glucose]/[mannitol] | $(10^3 \times)$ G/Na$^+$ | $(10^3 \times)$ M/Na$^+$ | G/M |
| 60 | 37.6 | 37.6 | 1.00 | 1.18 ± 0.54 | 1.29 ± 0.58 | 0.91 ± 0.02 |
| 120 | | | | 1.97 ± 0.46 | 2.13 ± 0.47 | 0.92 ± 0.02 |
| 180 | | | | 2.31 ± 0.39 | 2.53 ± 0.41 | 0.91 ± 0.03 |
| 240 | | | | 2.50 ± 0.34 | 2.73 ± 0.38 | 0.92 ± 0.04 |
| 300 | | | | 2.71 ± 0.36 | 2.98 ± 0.41 | 0.91 ± 0.02 |
| 360 | | | | 2.91 ± 0.26 | 3.15 ± 0.30 | 0.92 ± 0.01 |

TABLE XIV

Extracted flux ratios when the subdermal concentrations of glucose (G) and mannitol (M) were 7 mM and 3 mM, respectively (Experiment C, Example 6). Values are mean ± standard deviation.

| Time | Subdermal concentration ratios | | | Extracted flux ratios | | |
|---|---|---|---|---|---|---|
| (minutes) | $(10^3 \times)$ [G]/[Na$^+$] | $(10^3 \times)$ [M]/[Na$^+$] | [glucose]/[mannitol] | $(10^3 \times)$ G/Na$^+$ | $(10^3 \times)$ M/Na$^+$ | G/M |
| 60 | 52.6 | 22.5 | 2.33 | 1.79 ± 0.90 | 0.86 ± 0.45 | 2.09 ± 0.07 |
| 120 | | | | 2.86 ± 0.87 | 1.38 ± 0.46 | 2.09 ± 0.06 |
| 180 | | | | 3.35 ± 0.83 | 1.62 ± 0.44 | 2.08 ± 0.07 |
| 240 | | | | 3.57 ± 0.71 | 1.71 ± 0.39 | 2.11 ± 0.08 |
| 300 | | | | 3.77 ± 0.64 | 1.83 ± 0.40 | 2.08 ± 0.10 |
| 360 | | | | 3.99 ± 0.59 | 1.94 ± 0.36 | 2.07 ± 0.08 |

FIG. 22a shows the correlations between (a) the iontophoretic extraction ratio of glucose to sodium and the glucose sub-dermal concentration, and (b) the iontophoretic extraction ratio of mannitol to sodium and the mannitol sub-dermal concentration, following 6 hours of iontophoresis at 0.5 mA/cm$^2$.

FIG. 22b shows the correlations between (a) the iontophoretic extraction ratio of glucose to sodium and the sub-dermal concentration ratio (glucose/sodium), and (b) the iontophoretic extraction ratio of mannitol to sodium and the sub-dermal concentration ratio (mannitol/sodium), following 6 hours of iontophoresis at 0.5 mA/cm$^2$.

The overlap between the results for glucose and mannitol, presented in FIGS. 22a-b confirms the fact that mannitol can act as a model for the behaviour of glucose in reverse iontophoresis.

This point is emphasized in FIG. 22c which shows the almost perfect correlation between the iontophoretic extraction ratio of glucose to mannitol (following 6 hours of iontophoresis at 0.5 mA/cm$^2$) and the sub-dermal concentration ratio (glucose/mannitol).

The slope of the line of regression is close to unity.

Conclusions deduced earlier on the basis of mannitol data, therefore, are likely to be valid for glucose as well.

This example clearly shows that the reverse iontophoretic extraction of a neutral molecule (glucose) by electroosmosis can be "calibrated" by the use of an ionic internal standard (Na$^+$) which moves across the skin by electromigration.

Further, the results confirm that mannitol is a good model for glucose and that the method is applicable, therefore, to non-invasive glucose monitoring applications.

To illustrate how this technique would work in practice, consider some practical situations using the information and relationships obtained from the experiments described above.

Consider a hypothetical patient, whose NaCl concentration in plasma is 133 mM, on whom a reverse iontophoretic procedure is performed.

Suppose that analysis of the extracted samples indicates that 20 nmoles of glucose and 10 μmoles of sodium are extracted across 1 cm$^2$ of skin in 1 hour.

The extracted ratio (glucose/sodium) is $2 \times 10^{-3}$.

Now this information could be used in the following way:

Assume, in this hypothetical patient, that the glucose level below which hypoglycemia is a concern is 80 mg/dL (i.e., 4.4 mM).

This value corresponds to a molar ratio (glucose/sodium) of $33 \times 10^{-3}$ in the sub-dermal fluids assuming a constant sodium concentration of 133 mM.

According to our in vitro results (by substitution in the regression equation of FIG. 22a), an extraction ratio of $2 \times 10^{-3}$ indicates that the glucose concentration systemically is about 3.3 mM, i.e., the sub-dermal [glucose]/[sodium] ratio is $24.8 \times 10^{-3}$ (FIG. 22b).

We would conclude, therefore, that the glucose plasma levels of this patient were too low.

In fact, the values assumed for this hypothetical patient correspond closely to one of our in vitro experiments with a sub-dermal glucose concentration of 3 mM and a [mannitol]/[sodium] ratio of $22.5 \times 10^{-3}$.

In other words, there is a good predictive value of the equations developed.

A similar exercise could be performed, self-evidently, for a patient experiencing hyperglycemia (i.e., plasma glucose levels above a certain upper limit).

It is further important to reiterate that FIGS. 22a-b demonstrate the determination of the constants K and K' necessary to calculate an absolute concentration of an analyte in the biological system from the extracted ratio of the analyte to the chosen internal standard.

In this example, the chosen analyte (A) is glucose, while the internal standard (B) is $Na^+$.

According to Equation 1, therefore, $$Q\text{glu}/Q\text{Na}^+ = K \cdot [\text{glu}]/[\text{Na}^+]$$

K can be read from the slope of the graph in FIG. 22b; that is, following a period of iontophoresis of 6 hours at 0.5 mA/cm$^2$, K=0.076.

It is noteworthy that the corresponding value for mannitol, in this Example, is 0.078.

Similarly, according to Equation 2, $$Q\text{glu}/Q\text{Na}^+ = K' \cdot [\text{glu}]$$

K' can be read from the slope of the graph in FIG. 22a and is equal to K divided by the fixed $Na^+$ concentration (133 mM) in the biological system.

Following a period of iontophoresis of 6 hours at 0.5 mA/cm$^2$, K'=0.572×10$^{-3}$.

Note that the corresponding value for mannitol, in this Example, is 0.586×10$^{-3}$.

It follows that, once the value of K' has been established for a particular pair of substances, and given that the concentration of the internal standard ([B]) in the biological system is constant, then Equation 2 can be used to determine the concentration of the analyte of interest ([A]) directly from the iontophoretic extraction ratio Qa/Qb.

Finally, the linearity of the relationship established by the data in FIG. 22c indicates the possibility of using an uncharged molecule as an internal standard for an analyte which is also uncharged.

Example 7

Figure 23:
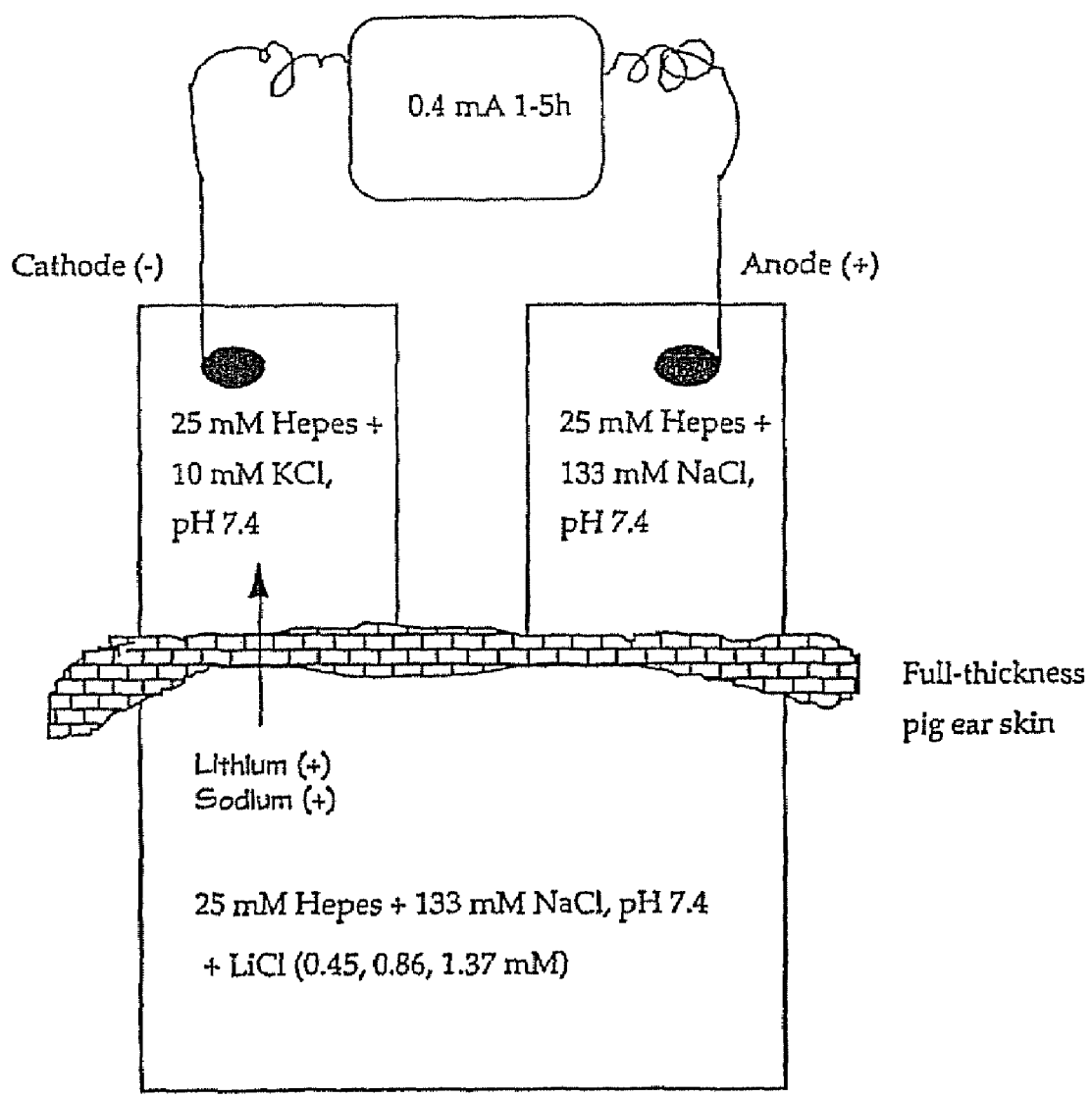
FIG. 23 represents a specifically-designed iontophoresis cell used for the in vitro experiments reported in Example 7

A series of in vitro experiments was performed in specifically-designed iontophoresis diffusion cells (Laboratory Glass Apparatus, Berkeley, Calif., USA) as represented in FIG. 23.

The sub-dermal (donor) solution was a pH 7.4 buffer (25 mM Hepes+133 mM NaCl) to which the analyte of interest, the anti-manic drug lithium (as the chloride salt) was added at one of 3 different concentrations: 1.37 mM, 0.86 mM, 0.45 mM.

Sodium ion was the chosen internal standard.

The anodal and cathodal chambers contacted the outer surface of the skin and contained the receptor (collection) media, respectively, 133 mM NaCl+25 mM Hepes and 10 mM KCl+25 mM Hepes (both buffered at pH 7.4).

Full-thickness pig-ear skin was clamped between the two halves of the iontophoresis cell and each chamber filled with the appropriate solution.

A schema of the experiment is shown in FIG. 23.

A current of 0.4 mA (0.5 mA/cm$^2$) was passed between silver-silver chloride, (Ag/AgCl) electrodes, inserted into the anodal and cathodal chambers, for a total of 5 hours.

Every hour, the entire content of the cathode solution was withdrawn and the chamber refilled with fresh buffer.

All samples were analyzed for lithium by atomic absorption spectroscopy and for sodium using an ion-selective electrode.

Three replicates were performed for each lithium concentration.

FIGS. 24a-b show the (a) the extraction fluxes of lithium and sodium, and (b) the (lithium/sodium) extraction flux ratios, over the 5 hours of experiment, for each sub-dermal lithium concentration considered.

Table XV also presents the extracted flux ratios (lithium/sodium), as a function of time, for each of the different sub-dermal concentration ratios (lithium/sodium) considered.

FIGS. 25a-b show the correlation between the iontophoretic extraction ratio of lithium to sodium and [a] the lithium sub-dermal concentration, and [b] the sub-dermal concentration ratio (lithium/sodium) over the 5-hour period of the experiment.

TABLE XV

Extracted flux ratios (×10$^3$) for lithium and sodium ions.
Values are mean ± standard deviation.

| | (10$^3$×) Extracted (lithium/Na$^+$) flux ratio (10$^3$×) Subdermal [lithium]/[Na$^+$] ratio | | |
|---|---|---|---|
| Time (min) | 3.4 | 6.5 | 10.3 |
| 60 | 0.71 ± 0.28 | 1.48 ± 0.41 | 2.28 ± 0.43 |
| 120 | 1.38 ± 0.19 | 2.65 ± 0.55 | 4.45 ± 0.64 |
| 180 | 1.54 ± 0.20 | 3.13 ± 0.78 | 5.25 ± 0.48 |
| 240 | 1.80 ± 0.03 | 2.79 ± 0.35 | 5.64 ± 0.52 |
| 300 | 1.62 ± 0.03 | 3.13 ± 0.51 | 5.45 ± 0.36 |

To illustrate how this technique would work in practice, consider some practical situations using the information and relationships obtained from the experiments described above.

Consider a patient taking lithium, whose plasma sodium concentration is 133 mM, and on whom a reverse iontophoretic procedure is performed.

Suppose that analysis of the extracted samples indicates that the extracted ratio (lithium/sodium) is 1×10$^{-3}$.

Now this information could be used in the following way:

Assume a therapeutic range for lithium of 0.5-1.4 mM.

Such values correspond to molar ratios (lithium/sodium) of 3.76×10$^{-3}$ and 10.5×10$^{-3}$ in the sub-dermal fluids.

According to our in vitro results (by substitution in the regression equation obtained at 5 hours, FIG. 25b), an extraction ratio of 1×10$^{-3}$ indicates that the sub-dermal [lithium]/[sodium] ratio is less than 3×10$^{-3}$, i.e., that the sub-dermal lithium concentration is less than 0.4 mM.

We would conclude, therefore, that the lithium plasma levels of this patient were too low and out of the therapeutic range.

It is further important to reiterate that FIGS. 25a-b demonstrate the determination of the constants K and K' necessary to calculate an absolute concentration of an analyte in the biological system from the extracted ratio of the analyte to the chosen internal standard.

In this example, the chosen analyte (A) is lithium, while the internal standard (B) is sodium.

According to Equation 1, therefore, $$Q\text{Li}/Q\text{Na} = K \cdot [\text{Li}]/[\text{Na}]$$

K is the slope of the graph in FIG. 25b; that is, following a short (5-hour) period of iontophoresis at 0.5 mA/cm$^2$, K=0.56.

Similarly, according to Equation 2, $$Q\text{Li}/Q\text{Na} = K' \cdot [\text{Li}]$$

K' is the slope of the graph in FIG. 25a and is equal to K divided by the fixed sodium concentration (133 mM) in the biological system.

Following a short (5-hour) period of iontophoresis at 0.5 mA/cm$^2$, K'=4.18×10$^{-3}$. It follows that, once the value of K' has been established for a particular pair of substances, and given that the concentration of the internal standard ([B]) in the biological system is constant, then Equation 2 can be used

Example 8

Two cylindrical glass cells (area=2 cm$^2$) were fixed to the ventral surface of a healthy volunteer's forearm. The distance between the chambers was approximately 8 cm.

The anode was positioned in one of the cells, which was filled with a solution containing a 10 mM Tris buffer pH 8:5+100 mM NaCl.

The other (collection) chamber contained the cathode submerged in a 10 mM Tris buffer at pH 8.5.

The two electrodes were connected to a power supply (Phoresor II Auto, Iomed, USA) and a current of 0.6 mA (0.3 mA/cm$^2$) was passed between them for a total of 5.5 hours.

The entire contents of the cathode solution were withdrawn every 15 minutes and the chamber was then refilled with fresh buffer.

From the seventh collection period, the volunteer's blood sugar concentration was measured at the beginning of each iontophoretic interval. A droplet of capillary blood was collected from the finger tip and analyzed for glucose with the Glucotrend 2 monitor (Roche Diagnostics, Switzerland).

Glucose in each iontophoretic sample was analyzed by high-performance anion-exchange chromatography with pulsed amperometric detection. Sodium ions were analyzed by an enzymatic β-galactosidase assay.

Figure 26:
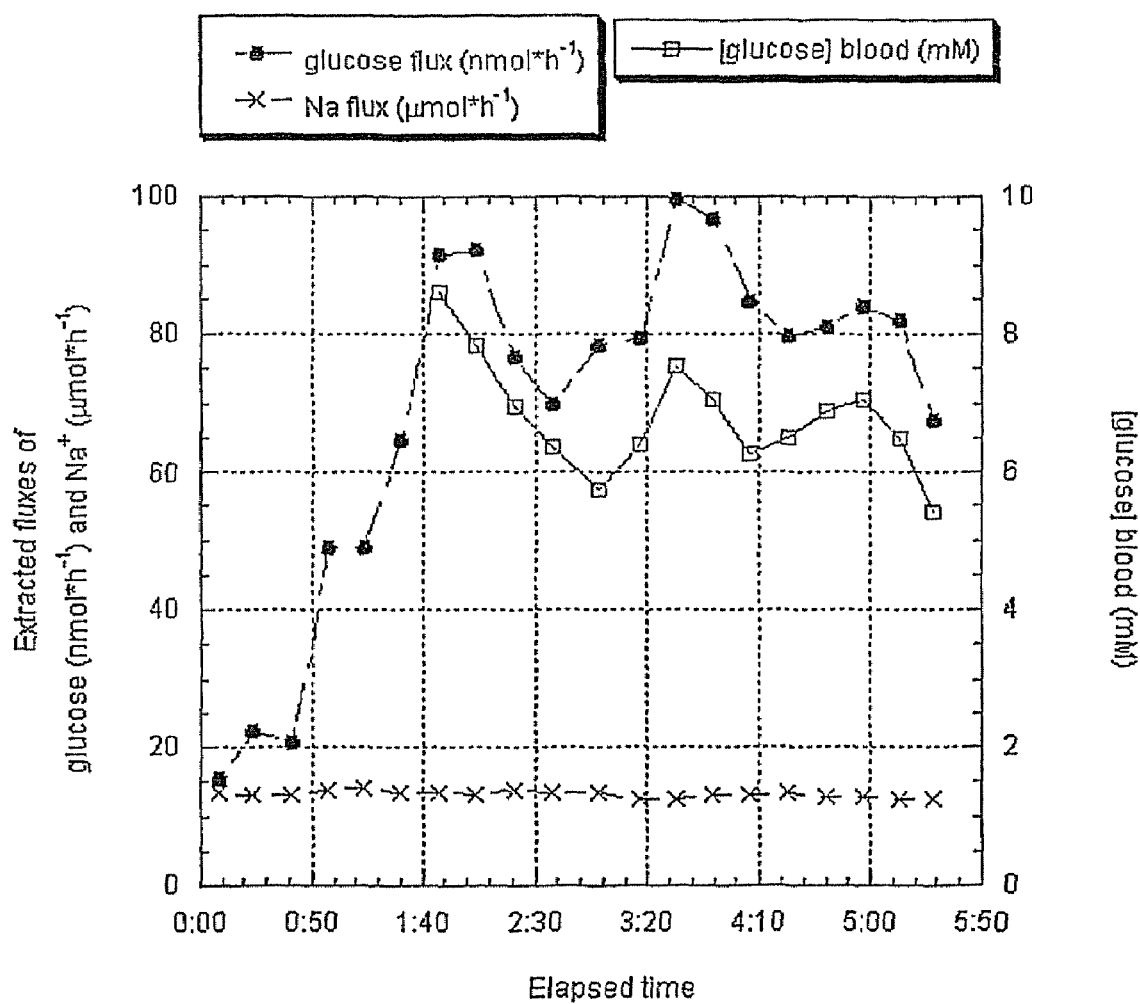
FIG. 26 shows the simultaneous extraction of glucose and sodium in vivo in a human being, and the correlation with the concentration of glucose in the blood.

FIG. 26 shows the results obtained. The blood glucose concentrations shown correspond to the average of the values measured at the beginning and at the end of each iontophoretic extraction period. The iontophoretically extracted glucose flux mirrored very closely the changes in blood sugar, increasing and then subsequently decreasing following ingestion of food. On the other hand, the extraction flux of Na$^+$ remained effectively constant over the entire period of the experiment, reflecting the fact that the systemic concentration of Na$^+$ is quite invariant in a living human being.

From the data in FIG. 26, it can be deduced that the ratio of the extracted flux of glucose divided by that of Na$^+$ depended linearly on both the blood concentration of glucose ($C_{glu}$):

$$J_{glu}/J_{Na^+} = 0.001 * C_{glu} - (1.6 \times 10^{-4}); r = 0.87$$

and on the ratio of the blood concentrations of glucose and Na$^+$ ($C_{glu}/C_{Na+}$):

$$J_{glu}/J_{Na^+} = 0.13 * (C_{glu}/C_{Na+}) + (7.2 \times 10^{-5}); r = 0.87$$

The data illustrate in vivo, in man, therefore, the principal features of the invention disclosed.

The invention claimed is:

1. A Iontophoretic sampling device for non-invasively monitoring the relative levels of two substances present in a biological system, said device comprising:
   an electrical power supply,
   a collection assembly comprising a first collection chamber containing a first electroconductive medium in contact with a first electrode and a second collection chamber containing a second electroconductive medium in contact with a second electrode, said electrodes being reversible electrodes and being each in contact with the electrical power supply when the collection assembly is inserted in the iontophoretic device;
   a means for analysing two or more selected charged and/or uncharged substances in either one or both of the collection chambers in order to determine their extracted amounts,
   a means for converting the extracted amounts of a first substance and a second substance to the extraction ratio of the first substance to the second substance, wherein said first and second substances are selected in such a way that the transport and/or transference number of the first substance is independent of the transport and/or transference number of the second substance.

2. The iontophoretic sampling device according to claim 1, characterised in that the electrodes are silver/silver chloride electrodes.

3. The iontophoretic sampling device according to claim 2, characterised in that the means for converting the extracted amounts of a first substance and a second substance to the extraction ratio of the first substance to the second substance is a programmable means able to calculate the ratio of the collected amount of the first extracted substance to the collected amount of the second extracted substance.

4. The iontophoretic sampling device according to claim 2, characterised in that the means for converting the extracted amounts of a first substance and of a second substance to the extraction ratio of the first substance to the second substance is a programmable means able to first calculate the flux of the first extracted substance and the flux of the second substance, based on the extracted amount of the first substance and the extracted amount of the second substance, respectively, and then to calculate the ratio of the flux of the first extracted substance to the flux of the second extracted substance.

5. The iontophoretic sampling device according to claim 4, characterised in that the analysis of the selected substances is made by techniques involving biosensing techniques.

6. The iontophoretic sampling device according to claim 5, characterised in that the first and second substances for which the extraction ratio is to be determined are susceptible to changes in their concentration in the biological system, so that relative levels of the first substance to the second substance are determined.

7. The iontophoretic device according to claim 5, characterised in that the first substance is susceptible to changes in its concentration in the biological system and the second substance has a substantially constant concentration in the biological system, so that the physiological concentration of the first substance is determined based upon the constant physiological concentration of the second substance.

8. The iontophoretic device according to claim 7, characterised in that the first substance is glucose.

9. The iontophoretic device according to claim 7, characterised in that the first substance is lithium.

10. The iontophoretic device according to claim 9, characterised in that the second substance is sodium.

11. The iontophoretic device according to claim 10, characterised in that it further comprises a means to reverse the electrode polarity subsequent to each extraction/analysis cycle.

12. The iontophoretic device according to claim 11, characterised in that it is miniaturised to be worn on a person's body.

* * * * *